United States Patent [19]
Liu et al.

[11] Patent Number: 5,108,919
[45] Date of Patent: Apr. 28, 1992

[54] DNA SEQUENCES ENCODING YEAST UBIQUITIN HYDROLASE

[75] Inventors: Chung-Cheng Liu, Foster City; Harvey I. Miller, Pleasant Hill, both of Calif.

[73] Assignee: Genentech, Inc., South San Francisco, Calif.

[21] Appl. No.: 284,281

[22] Filed: Dec. 14, 1988

Related U.S. Application Data

[63] Continuation-in-part of Ser. No. 210,909, Jun. 24, 1988.

[51] Int. Cl.$^5$ .................. C12N 9/60; C12N 15/00; C07H 15/12
[52] U.S. Cl. ................... 435/224; 435/172.3; 435/240.2; 435/252.33; 435/252.3; 435/255; 435/320.1; 536/27
[58] Field of Search .............. 435/91, 195, 224, 240.1, 435/252.3, 252.33, 255, 320; 536/27

[56] References Cited

U.S. PATENT DOCUMENTS

| | | | |
|---|---|---|---|
| 4,757,013 | 7/1988 | Inouye et al. | 435/172.3 |
| 4,771,002 | 9/1988 | Gelvin | 435/252.33 |

FOREIGN PATENT DOCUMENTS

| | | | |
|---|---|---|---|
| 150126 | 7/1985 | European Pat. Off. | |
| WO8802406 | 4/1988 | PCT Int'l Appl. | 435/172.3 |
| WO8807085 | 9/1988 | PCT Int'l Appl. | |

OTHER PUBLICATIONS

Day et al. (1987), "Molecular Cloning of cDNA coding for Human PGP 9.5", FEB Letters, vol. 210, pp. 157–160.
Matsui et al. (1982), "Isopeptidase", PNAS, vol. 79, pp. 1535–1539.
Okayama et al. (1983), "A cDNA Cloning Vector", MCB, vol. 3, pp. 280–289.
Wood (1987), "Gene Cloning Based on Long Oligonucleotide Probes", in Methods in Enzymology, vol. 1542 (Academic Press, N.Y.), pp. 443–447.
Kanda et al. (1986), "Substrate Recognition of Isopeptidase", BBA, vol. 870, 64–75.
Rechsteiner, "Ubiquitin-Mediated Pathways for Intracellular Proteolysis", Ann. Rev. Cell Biol., 3: 1–30 (1987).
Rechsteiner, M., Ubiquitin, Chapters 2, 5, and 6 (N.Y.: Plenium Press, 1988).
Ozkaynak et al., "The Yeast Ubiquitin Genes: a Family of Natural Gene Fusions", pp. 1429–1439, The EMBO Journal, 6: (1987).
Lund et al., "Nucleotide Sequence Analysis of a cDNA Encoding Human Ubiquitin Reveals that Ubiquitin is Synthesized as a Precursor", J. Biol. Chem., vol. 260, pp. 7609–7613 (1985).
Barr et al., "Production of Recombinant DNA-Derived Pharmaceuticals in the Yeast Saccharomyces Cerevisiae", Abst. 34, Amer. Chem. Soc., Sep. 25–30, 1988.
Bachmair et al., Science, 234: 179–186 (1986).
Butt et al., PNAS U.S.A., 86: 2540–2544 (1989).
Hough et al., J. Biol. Chem., 261 (5): 2400–2406 (1986).
Mayer & Wilkinson, Biochemistry, 28: 166–172 (1989).
Duerksen-Hughes et al., Biochemistry, 28: 8530–8536 (1989).
Wilkinson et al., Science, 246: 670–673 (1989).
Pickart and Rose, "Mechanism of Ubiquitin Carboxyl-Terminal Hydrolase", pp. 10210–10217, vol. 261 (Aug. 1986) The Journal of Biological Chemistry.
Pickart and Rose, J. Biol. Chem., 260 (13): 7903–7910 (1985).

Primary Examiner—Richard A. Schwartz
Assistant Examiner—Richard M. Lebovitz
Attorney, Agent, or Firm—Janet E. Hasak

[57] ABSTRACT

A ubiquitin hydrolase is provided having a purity of at least 70% homogeneity based on the weight of the total protein in the composition. Also provided are DNA sequences encoding ubiquitin hydrolases, as well as expression systems for their recombinant production. Processes are provided for purification of a ubiquitin hydrolase from eukaryotes and for its use in recovering any desired polypeptide free from its fusion at its N-terminus with ubiquitin.

25 Claims, 29 Drawing Sheets

Fig.1a-1.

```
                                                    mseI              hphI  ddeI     mnlI
      xbaI                                          TTAACAGGCA AGACTATCAC CTTAGAGGTT
  1  5'-CTAGAATTA TGCAAATTTT CGTCAAAACT
  3'-    TTAAT ACGTTTAAAA GCAGTTTTGA AATTGTCCGT TCTGATAGTG GAATCTCCAA
          M etGlnIlePh eValLysThr LeuThrGlyL ysThrIleTh rLeuGluVal mboII                                                            bspMII
          hinfI    taqI                                                    mnlI
 61       GAATCTTCCG ACACTATCGA TAACGTCAAA TCTAAAATTC AAGATAAAGA AGGTATCCCT
          CTTAGAAGGC TGTGATAGCT ATTGCAGTTT AGATTTTAAG TTCTATTTCT TCCATAGGGA
 18       GluSerSerA spThrIleAs pAsnValLys SerLysIleG lnAspLysGl uGlyIlePro sau3AI
          dpnI
          alwI
          mspI                                            mboII   rsaI
          hpaII                                                                    ecoRI
121       CCGGATCAAC AGCGTTTGAT TTTTGCTGGT AAGCAACTAG AAGATGGTCG TACCTTGTCT
          GGCCTAGTTG TCGCAAACTA AAAACGACCA TTCGTTGATC TTCTACCAGC ATGGAACAGA
 38       ProAspGlnG lnArgLeuIl ePheAlaGly LysGlnLeuG luAspGlyAr gThrLeuSer taqI
                   salI
                   hincII
                   accI  mboII
              pleI pleI
              hinfI hinfI draIII              hgaI     hphI
          fokI                                                                     ecoRI
181       GACTACAACA TCCAAAAGGA GTCGACTCTT CACTTGGTGT TGCGTCTCCG TGGTGGTGAA
          CTGATGTTGT AGGTTTTCCT CAGCTGAGAA GTGAACCACA ACGCAGAGGC ACCACCACTT
 58       AspTyrAsnI leGlnLysGl uSerThrLeu HisLeuValL euArgLeuAr gGlyGlyGlu
```

```
                    taqI
                          fokI  mboII           xmnI
241 TTCATCGAAG GTCGTTCTTG GATGGAAGAA GTTATCAAAC TGTGCGGTCG TGAACTGGTT
    AAGTAGCTTC CAGCAAGAAC CTACCTTCTT CAATAGTTTG ACACGCCAGC ACTTGACCAA
78  PheIleGluG lyArgSerTr pMetGluGlu ValIleLysL euCysGlyAr gGluLeuVal sau3AI                                              mnlI
                                                                  sau3AI
          ddeI                            scrFI                   dpnI
       hgiAI  dpnI                        bstNI                   alwI
       bsp1286       accI                                    xhoII xbaI
301 CGTGCTCAGA TCGCTATCTG CGGTATGTCT ACCTGGTCTA AACGTTCTCT GTAAGATCCT
    GCACGAGTCT AGCGATAGAC GCCATACAGA TGGACCAGAT TTGCAAGAGA CATTCTAGGA
98  ArgAlaGlnI leAlaIleCy sGlyMetSer ThrTrpSerL ysArgSerLe uOC* taqI
       salI
       hincII  fnu4HI
       accI    bbvI
       pleI    pstI        aluI
       hinfI   bspMI       hindIII
361 CTAGAGTCGA CCTGCAGCCC A          -3'
    GATCTCAGCT GGACGTCGGG TTCGA      -5'
```

```
                                                         pleI
                                                         hinfI
                          draIII      hgaI               hphI
              5'-          GTGT TGCGTCTCCG TGGTGGTGAC
              3'-          AACCACA ACGCAGAGGC ACCACCACTG
                  HisLeuValL euArgLeuAr gGlyGlyAsp hinPI
                                              hhaI
                          fnu4HI              thaI
                          haeIII              hinPI
                          xmaI                hhaI
                          eaeI                bssHII
                          notI   thaI         thaI
                          fnu4HI xmoI
              CAAACTGTGC GGCCGCGAAT TAGTTCGCGC GCAGATTGCC
              GTTTGACACG CCGGCGCTTA ATCAAGCGCG CGTCTAACGG
              eLysLeuCys GlyArgGluL euValArgAl aGlnIleAla nlaIII
                   scrFI                   styI    sfaNI   ddeI
                   hgiAI                   ncoI   mboII    mnlI
              nlaIII  bstNI
              fnu4HI  bsp1286
      fokI mboII
  241 TCTTGGATGG AAGAAGTTAT CAAACTGTGC GGCCGCGAAT TAGTTCGCGC GCAGATTGCC
      AGAACCTACC TTCTTCAATA GTTTGACACG CCGGCGCTTA ATCAAGCGCG CGTCTAACGG
   78 SerTrpMetG luGluValIl eLysLeuCys GlyArgGluL euValArgAl aGlnIleAla 301 ATTTGCGGCA TGAGCACCTG GAGCAAAAGG TCTCTGTAGC CATGGAAGAT GCTCCTCAGA
      TAAACGCCGT ACTCGTGGAC CTCGTTTTCC AGAGACATCG GTACCTTCTA CGAGGAGTCT
   98 IleCysGlyM etSerThrTr pSerLysArg SerLeuAM*P roTrpLys
                                                   fokI
  361 CACCTAGACC AGTGGCAGAA ATTGTGCCAT CCTTCATCAA CAAAGATACA GAAACCATAA
      GTGGATCTGG TCACCGTCTT TAACACGGTA GGAAGTAGTT GTTTCTATGT CTTTGGTATT
```

```
                                                                    taqI
                                                                    aluI
                                                         rsaI       sacI
                                                         nlaIV      hgiAI
                                                         kpnI       bsp1286
                                              aluI       banI       banII
                                              alwNI
421  ATATGATGTC AGAATTTGTT GCTAATTGCT CACAGGAGCT GAAGTTGGGT ACCGAGCTCG
     TATACTACAG TCTTAAACAA CGATTAAACG GTGTCCTCGA CTTCAACCCA TGGCTCGAGC hgiAI
                                                              bsp1286
                                 ddeI    aluI                 apaLI
     sau3AI
     dpnI
     xhoII
     bglII
481  AATTCGCAAA ACCTAGCAAG AGATCTCTTG CTAGATTTTG CTGAGATGAA GCTAATTGTG
     TTAAGCGTTT TGGATCGTTC TCTAGAGAAC GATCTAAAAC GACTCTACTT CGATTAACAC sfaNI
     sspI                     mseI
541  CACATCTCGT ATAATATTCA CACATATTCT TAATGACATT TCACTGATGC TTCTATCAGG
     GTGTAGAGCA TATTATAAGT GTGTATAAGA ATTACTGTAA AGTGACTACG AAGATAGTCC mseI
                      taqI   aluI
     nlaIII    aluI   claI   hindIII       -3'
601  TCAATTCTCA TGTTTGACAG CTTATCATCG ATA           -5'
     AGTTAAGAGT ACAAACTGTC GAATAGTAGC TATTCGA
```

```
    taqI
    salI                                                           sau3AI
    hincII                   mseI                                  dpnI
    accI                     aflII              mseI               bclI
  1 GT CGACTATAAA GGTGGAAGTC CATACTTAAG AGATATTAAG GGTATTTGA TCAACAAGTA
    CA GCTGATATTT CCACCTTCAG GTATGAATTC TCTATAATTC CCATAAAACT AGTTGTTCAT nlaIV
                                                                   banI
 63 AGTAACAATC GTTATAAAAA TACAATAGCA AAAGTATGAG CGGAGAAAAT CGTGCTGTGG
    TCATTGTTAG CAATATTTT ATGTTATCGT TTTCATACTC GCCTCTTTTA GCACGACACC
  1                                              MetSe rGlyGluAsn ArgAlaValVal mseI
                                                          draI
           hinfI                                          ahaIII
123 TGCCGATTGA ATCAAACCCT GAAGTTTTA CAAATTTTGC ACATAAATTA GGTTTAAAAA
    ACGGCTAACT TAGTTTGGGA CTTCAAAAT GTTTAAAACG TGTATTTAAT CCAAATTTTT
 10 ProIleGl uSerAsnPro GluValPheT hrAsnPheAl aHisLysLeu GlyLeuLysAsn ecoRV                                          bsmI     styI
            taqI       aluI
183 ATGAATGGGC GTATTTCGAT ATCTATAGCT TAACAGAGCC AGAGTTACTA GCATTCTTAC
    TACTTACCCG CATAAAGCTA TAGATATCGA ATTGTCTCGG TCTCAATGAT CGTAAGAATG
 30 GluTrpAl aTyrPheAsp IleTyrSerL euThrGluPr oGluLeuLeu AlaPheLeuPro rsaI
    haeIII   haeIII       fnu4HI                          mnlI     taqI
    haeI     haeI         bbvI
243 CAAGGCCAGT GAAGGCCATT GTGCTGCTAT TTCCGATAAA CGAGGATAGA AAATCGAGTA
    GTTCCGGTCA CTTCCGGTAA CACGACGATA AAGGCTATTT GCTCCTATCT TTTAGCTCAT
 50 ArgProVa lLysAlaIle ValLeuLeuP heProIleAs nGluAspArg LysSerSerThr
```

Fig.3b.

```
              hincII                          mseI
303 CCAGTCAACA AATTACAAGT TCTTATGATG TTATATGGTT TAAGCAATCA GTCAAAAATG
    GGTCAGTTGT TTAATGTTCA AGAATACTAC AATATACCAA ATTCGTTAGT CAGTTTTTAC
 70  SerGlnGl  nIleThrSer SerTyrAspV alIleTrpPh eLysGlnSer ValLysAsnAla
                                                             mspI
                                                             hpaII
                                                             scrFI
                                                             ncII
                                                          bsp1286
                                                          banII
                                                       nlaIV   nlaIV
              mboII
363 CGTGCGGATT GTATGCAATT CTTCATTCTT TGAGCAATAA CCAGTCATTG TTGGAGCCCG
    GCACGCCTAA CATACGTTAA GAAGTAAGAA ACTCGTTATT GGTCAGTAAC AACCTCGGGC
 90  CysGlyLe  uTyrAlaIle LeuHisSerL euSerAsnAs nGlnSerLeu LeuGluProGly
         mseI                                         taqI
         draI                                         aluI mboII
         ahaIII
423 GCTCCGACTT GGACAATTTT TTAAAATCTC AAAGTGATAC TTCAAGCTCG AAGAATAGGT
    CGAGGCTGAA CCTGTTAAAA AATTTTAGAG TTTCACTATG AAGTTCGAGC TTCTTATCCA
110  SerAspLe  uAspAsnPhe LeuLysSerG lnSerAspTh rSerSerSer LysAsnArgPhe
                                                                rsaI
483 TTGATGATGT TACTACCGAC CAATTCGTCT TGAATGTAAT AAAAGAGAAT GTACAAACAT
    AACTACTACA ATGATGGCTG GTTAAGCAGA ACTTACATTA TTTTCTCTTA CATGTTTGTA
130  AspAspVa  lThrThrAsp GlnPheValL euAsnValIl eLysGluAsn ValGlnThrPhe
```

Fig. 3c.

```
                    haeIII                                                    pstI
                    haeI
                    eaeI
                    balI
543   TTTCTACTGG CCAGTCAGAA GCACCAGAAG CAACTGCAGA TACTAATCTA CACTATATCA
      AAAGATGACC GGTCAGTCTT CGTGGTCTTC GTTGACGTCT ATGATTAGAT GTGATATAGT
150     SerThrGl   yGlnSerGlu  AlaProGlu  AlaThrAlaAs  pThrAsnLeu  HisTyrIleThr sau96I
                                                                        nlaIV
      ndeI  mboII      mnlI              fokI                           avaII mnlI
603   CATATGTGGA AGAGAACGGA GGGATATTTG AACTGGATGG AAGGAATTTG AGCGGACCCC
      GTATACACCT TCTCTTGCCT CCCTATAAAC TTGACCTACC TTCCTTAAAC TCGCCTGGGG
170     TyrValGl   uGluAsnGly  GlyIlePheG  luLeuAspGl  uArgAsnLeu  SerGlyProLeu Ub-17 Probe I
663   TCTATTTGGG AAAGAGTGAC CCAACTGCCA CCGATTTGAT TGAACAGGAA TTAGTTAGAG
      AGATAAACCC TTTCTCACTG GGTTGACGGT GGCTAAACTA ACTTGTCCTT AATCAATCTC
190     TyrLeuGl   yLysSerAsp  ProThrAlaT  hrAspLeuIl  eGluGlnGlu  LeuValArgVal pleI                        mboII
       hinfI mnlI                  mboII              mseI
723   TGAGAGTCGC CTCATATATG GAAAATGCAA ATGAAGAAGA TACTTCTTCT TGTATTAAAC TTTGCTATGC
      ACTCTCAGCG GAGTATATAC CTTTTACGTT TACTTCTTCT ATGAAGAAGA ACATAATTTG AAACGATACG
210     ArgValAl   aSerTyrMet  GluAsnAlaA  snGluGluAs  pThrSerSer  pValLeuAsn  PheAlaMetLeu
```

Fig. 3d.

```
         sau96I
         haeIII
         sau96I
         nlaIV
         ecoO
         bsp1286
         banII
         apaI
 783 TAGGATTGGG CCCTAATTGG GAATAATAAT TGTTTTATTA CTGCGTAGTC AAATATGTAT
     ATCCTAACCC GGGATTAACC CTTATTATTA ACAAAATAAT GACGCATCAG TTTATACATA
 230  GlyLeuGl yProAsnTrp GluOC* mseI
             draI
       ecoRI ahaIII            hphI
 843 TTACAGAATT CTTTTAAATA TATAATTCAC CTACTCATCA TAGCCACCGC CAAAAGAAAG
     AATGTCTTAA GAAAATTTAT ATATTAAGTG GATGAGTAGT ATCGGTGGCG GTTTTCTTTC taqI
       mnlI                    taqI       claI
 903 GAAACCTCCA GTTTGTCTGG AATGTCTCGA AAAATAATCG AAATCGATGG ACACAGCGTT
     CTTTGGAGGT CAAACAGACC TTACAGAGCT TTTTATTAGC TTTAGCTACC TGTGTCGCAA sau3AI
             dpnI              rsaI             sfaNI
       sau96I alwI             scaI      ddeI   ddeI
       haeIII
 963 TGCTAATAAC ACGGCCCTTT GATCCAAAGT TAGTACTTGA GAACTTAGCA TCTCAGTAGG
     ACGATTATTG TGCCGGGAAA CTAGGTTTCA ATCATGAACT CTTGAATCGT AGAGTCATCC sspI     sfaNI   hinfI         fau4HI
1023 ATAAATATTA TCAAAGCATC TCTGCGAATC AAATCT C  CATAAACAC CAGTAT~300 →BamHI
     TATTTATAAT AGTTTCGTAG AGACGCTTAG TTTAGA G  GTATTTGTG GTCATA
```

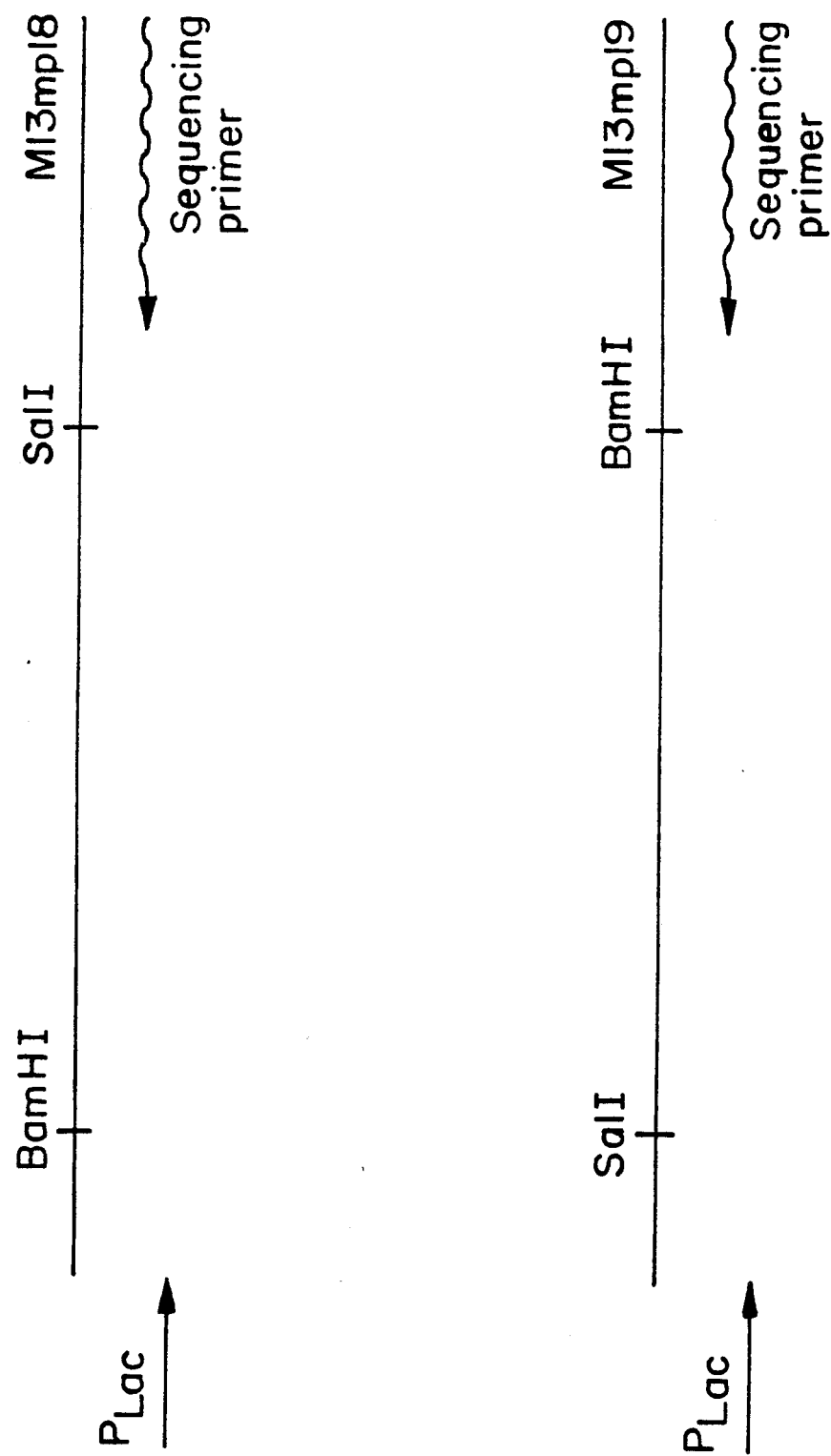

Fig. 5A.

```
CCTTGTCACTATGCGCTGTCTTTTCTACTTTATTGCTTATAACTCTTGCACCTCCAATCAAGG

TATCCACTTTCTCCATTGTATCCAATTCACCTTCGCTTTCATTTACGAAAAAAAGCTTACATCA
                                                   HindIII

CTACCACTATCACTTGAATCAGAAAGACATTGCTTGTTATATTTATCATTATCGGAAATAAGATC

AGTAGCCGGAGTTGCCATCATTGTAATACTCCCCAGTTAACCTCTACAAGTTGATTCTTTTACGT

ATCACCAAAATAGGCAGGCTATTCTTACCCAGTCCTTTCTTTTTAAGGGCGTCATAGAGTTGTAA

GCATTTTTTGAGAATGCAGTGATGAGCTATTAACTTCTCAAAACTTCCTGACGTTTATTACCCG

GATTGAAGTACCTTGTATTCTTGGAGATGTCTGTGGTCGAGTTAGGAAGTGTGAACATGCCTATC

AACGCCCCAAAAACCAGTGCAGATAATGATCTGAACAATTTTCCGTGTTTAAACTTCCTCAG
        SalI
TAGAAGTATTTTTATTTAGTCGACTATAAAGGTGGAAGTCCATACTTAAGAGATATTAAGGGTAT 1
                                          met ser gly glu
TTTGATCAACAAGTAAGTAACAATCGTTATAAAAATACAATAGCAAAAGT ATG AGC GGA GAA 10                             20
asn arg ala val val pro ile glu ser asn pro glu val phe thr asn phe
AAT CGT GCT GTG GTG CCG ATT GAA TCA AAC CCT GAA GTT TTT ACA AAT TTT
```

Fig. 5B.

```
                peptide 14         *30    *     *      *     *   EcoRV
ala his lys leu gly leu lys asn glu tyr ala tyr phe asp ile tyr ser
GCA CAT AAA TTA GGT TTA AAA AAT GAA TGG GCG TAT TTC GAT ATC TAT AGC
              40                                50
leu thr glu pro glu leu leu ala phe leu pro arg pro val lys ala ile
TTA ACA GAG CCA GAG CTA GCA TTC CTA CCA AGG CCA GTG AAG GCC ATT
              60                                           70
val leu leu phe pro ile asn glu asp arg lys ser ser thr ser gln gln
GTG CTG CTA TTT CCG ATA AAC GAG GAT AGA AAA TCG AGT ACC AGT CAA CAA
                              80
ile thr ser ser tyr asp val ile trp phe lys gln ser val lys asn ala
ATT ACA AGT TCT TAT GAT GTT ATA TGG TTT AAG CAA TCA GTC AAA AAT GCG
         90                              100
cys gly leu tyr ala ile leu his ser leu ser asn asn gln ser leu leu
TGC GGA TTG TAT GCA ATT CTT CAT TCT TTG AGC AAT AAC CAG TCA TTG TTG
                                                    120
glu pro gly asp ser asp leu asp asn phe leu lys ser gln ser asp thr ser
GAG CCC GGC TCC GAC TTG GAC AAT TTT TTA AAA TCT CAA AGT GAT ACT TCA
peptide 8    *     *   130   *     *     *                      140
ser ser lys asn arg phe asp asp val thr thr asp gln phe val leu asn
AGC TCG AAG AAT AGG TTT GAT GAT GTT ACT ACC GAC CAA TTC GTC TTG AAT
```

Fig.5C.

```
     val ile lys glu asn val gln thr phe ser thr gly gln ser glu ala pro
     GTA ATA AAA GAG AAT GTA CAA ACA TTT TCT ACT GGC CAG TCA GAA GCA CCA
                          150
                                                          170
     glu ala thr ala asp thr asn leu his tyr ile thr tyr val glu glu asn
     GAA GCA ACT GCA GAT ACT AAT CTA CAC TAT ATC ACA TAT GTG GAA GAG AAC
              160
                                                                  190 pept
     gly gly ile phe glu leu asp gly arg asn leu ser gly pro leu tyr leu
     GGA GGG ATA TTT GAA CTG GAT GGA AGG AAT TTG AGC GGA CCC CTC TAT TTG
                      180
     ide 17  *       *       *       *   200  *       *       *       *
     gly lys ser asp pro thr ala thr asp leu ile glu gln glu leu val arg
     GGA AAG AGT GAC CCA ACT GCC ACC GAT TTG ATT GAA CAG GAA TTA GTT AGA
                 GAC CCA ACT GCt ACt GAC TTG ATc GAA CAa TTg GTT AGA
      *  210  *       *          (PROBE)
     val arg val ala ser tyr met glu asn ala asn glu glu asp val leu asn
     GTG AGA GTC GCC TCA TAT ATG GAA AAT GCA AAT GAA GAA GAT GTA TTA AAC
                                                      220
                             236
     phe ala met leu gly leu gly pro asn trp glu oc
     TTT GCT ATG CTA GGA TTG GGC CCT AAT TGG GAA TAA
                         230
                                                   EcoRI
     TAATTGTTTTATTACTGCGTAGTCAAATATGTATTTACAGAATTCTTTTAAATATATAATTCACC
```

```
TACTCATCATAGCCACCGCCAAAAGAAAGGAAACCTCCAGTTTGTCTGGAATGTCTCGAAAAATA

ATCGAAATCGATGGAGACACAGCGTTTGCTAATAACACGGCCCTTTGATCCAAAGTTAGTACTTGAG

AACTTAGCATCTCAGTAGGATAAATATTATCAAAGCATCTCTGCGAATCAAATCTAACAACATAA

ACACCAGTATCGGTAAACATTTCTCTTCCTAAACCAATTTCTGTCTACACTCGCCATTAT

CTTACCATCAGCATCTGTTACAGGAAAATCAAATGATAAGAAAGGTGCATCTATCTTACCAAATT
      BamHI
      GGTCAAAAGTGGATCC
```

Fig. 5D.

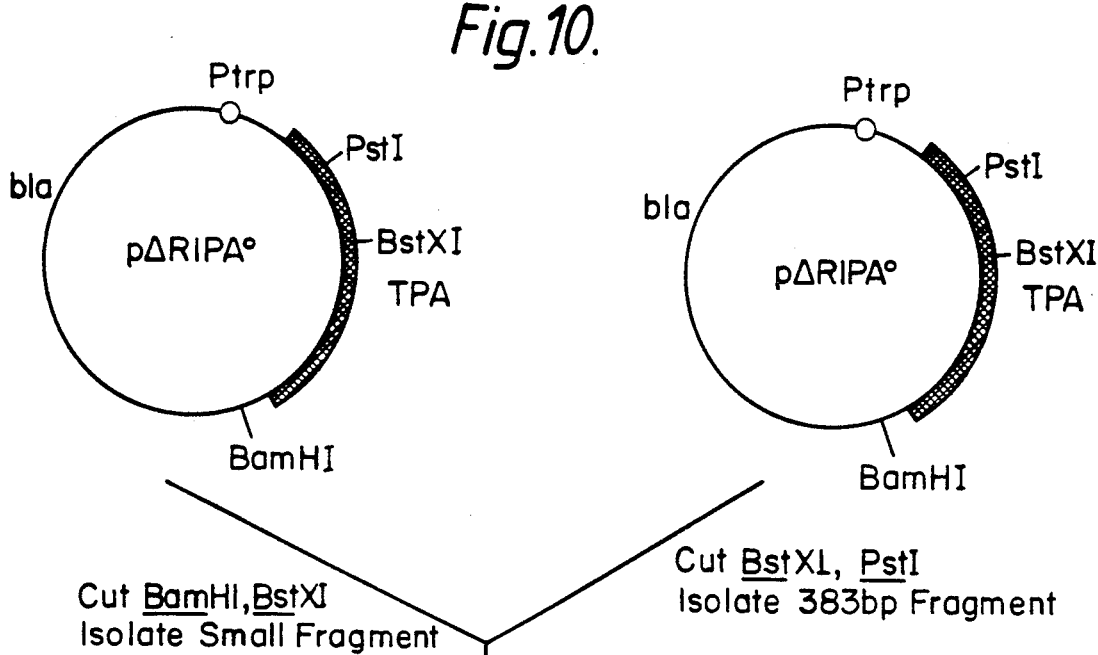
Fig. 10.
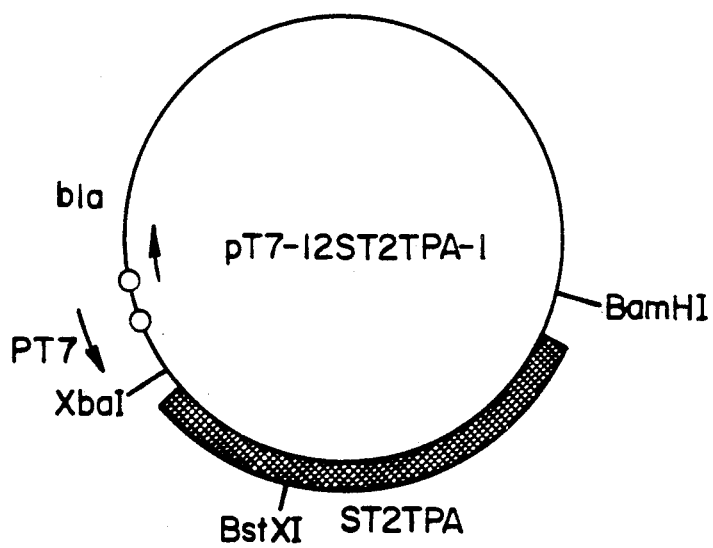

Fig.18.
B    a   b   c   d
1.95— 
.85— 

DNA SEQUENCES ENCODING YEAST UBIQUITIN HYDROLASE

This application is a continuation-in-part application of copending U.S. Ser. No. 07/210,909 file Jun. 24, 1988.

BACKGROUND OF THE INVENTION

This invention relates to the purification of ubiquitin hydrolases having enzymatic activity in cleaving ubiquitin-protein conjugates. This invention also relates to a process for preparing ubiquitin hydrolases using recombinant methods and a process for using same to isolate polypeptides from fusions thereof with ubiquitin.

The polypeptide known as ubiquitin is highly conserved, has a molecular weight of 8,565, and contains 76 amino acid residues. It is encoded by genes that contain varying numbers of the protein sequence repeated without any stop codons between them or with other proteins. Ubiquitin is reviewed in Rechsteiner, *Ann. Rev. Cell. Biol.*, 3: 1-30 (1987) and in Rechsteiner, M., ed., *Ubiquitin* (New York: Plenum Press 1988).

Ubiquitin was first purified during studies of peptides of the thymus. Radioimmunoassays for the peptide revealed that it was found widely in plant, animal, and yeast. Goldstein et al., *Proc. Natl. Acad. Sci. U.S.A.* 72: 11-15 (1975). The sequence of amino acids 1-74 of thymus ubiquitin was determined by Schlesinger et al., *Biochemistry*, 14: 2214-2218 (1975), revealing an $NH_2$-terminal methionine and an arginine at position 74. The sequence was confirmed by Low et al., *J. Biol. Chem.*, 254: 987-995 (1979). This form was later shown to be a degraded form of ubiquitin and is not active in its biological function. The active form is the 76 amino acid form. Wilkinson and Audhya, *J. Biol. Chem.*, 256: 9235-9241 (1981).

It has been found that ubiquitin is involved in the energy-dependent degradation of intracellular proteins. Ganoth et al., *J. Biol. Chem.*, 263: 12412-12419 (1988). Evidence exists that in eukaryotes, covalent conjugation of ubiquitin to the proteins is essential for their selective degradation. Finley and Varshavsky, *Trends Biochem. Sci.*, 10: 343-346 (1985) and Finley et al., *Cell*, 37: 43 (1984).

Isopeptidases have been identified that are unique for eukaryotes. They are found to cleave in vitro an amide bond formed between a ubiquitin Gly-COOH terminal and epsilon-$NH_2$ group of lysine on other polypeptides. For example, an isopeptidase was identified that cleaves the linkage between ubiquitin and lysozyme to yield free lysozyme. Hershko et al., *Proc. Natl. Acad. Sci. U.S.A.*, 81: 1619-1623 (1984). An isopeptidase was also detected in reticulocyte extracts that cleaves ubiquitin-histone 2A conjugates, with the release of undegraded histone. Andersen et al., *Biochemistry*, 20: 1100-1104 (1981), Kanda et al., *Biochim. Biophys. Acta*, 870: 64-75 (1986), Matsui et al., *J. Cell biol.*, 95: (2) PA82 (1982), and Matsui et al., *Proc. Natl. Acad. Sci. U.S.A.*, 79: 1535-1539 (1982). See also Hershko et al., *Proc. Natl. Acad. Sci.* U.S.A., 77: 1783-1786 (1980) and Haas and Rose, *Proc. Natl. Acad. Sci.* U.S.A., 78: 6845-6848 (1981). *Isopeptidase was purified* 175-fold from calf thymus by ion-exchange chromatography, gel filtration, and affinity chromatography on whole histone and histone H2A Sepharose. Kanda et al., *J. Cell Biol.*, 99: (4), PA135 (1984). This purified isopeptidase was found to be specific to the epsilon-(glycyl)lysine linkage in structural chromatin protein A24.

When the isopeptidase was purified, it was found to exist in growing Chinese hamster cells as two major forms having molecular weight 250,000 and 34,000, but was found to be present in human erythrocytes and calf thymus only in the 250,000 molecular weight form. These two forms of enzyme were found to be distinct from one another, in that the degradation of the large form did not result in the appearance of the smaller form. Matsui, *J. Cell Biol.*, 105: (4 Part 2), 187A (1987). The author suggests that the large form is a stable constitutive enzyme and that the small form with a rapid turnover rate is linked to the metabolic pathway of growth-related ubiquitin-protein conjugates. Isopeptidase activity of 30 kDa on silver-stained SDS-PAGE (called carboxyl-terminal hydrolase) was also identified in human red blood cells. Pickart and Rose, *J. Biol. Chem.*, 260: 7903-7910 (1985). The same enzyme may be involved in the cleavage as is involved in processing the ubiquitin-protein fusions. Pickart and Rose, *J. Biol. Chem.*, 261: 10210-10217 (1986). This enzyme was formerly called ubiquitin carboxyl-terminal esterase because it was found to hydrolyze ubiquitin esters of small thiols. Rose and Warms, *Biochemistry*, 22: 4234-4237 (1983).

An activity of processing protease is reported in WO 88/02406 published Apr. 7, 1988, in the context of designing or modifying specified amino termini based on introducing the use of artificial ubiquitin-protein fusions.

Ubiquitin aldehyde was found to form strong complexes with most hydrolases, e.g., the major ubiquitin-protein hydrolase of greater than 200 KDa, a small 30 KDa cationic hydrolase, and the major hydrolase of 30 KDa that acts on small molecule conjugates of ubiquitin. Rose et al., *Fed. Proc.*, 46: (6), 2087 (1987). It was concluded that ubiquitin hydrolases, in addition to being important in rescuing ubiquitin from traps with small nucleophiles, are necessary for recycling ubiquitin from protein conjugates that are only slowly degraded.

Recent analysis of the genes encoding ubiquitin from various organisms by molecular genetic techniques has shown that ubiquitin is synthesized as a polyubiquitin precursor with multiple, contiguous stretches of ubiquitin sequences or as a protein fusion in which ubiquitin is located at the N-terminal domain of a larger protein. Ozkaynak et al., *The EMBO J.*, 6: 1429-1439 (1987); Lund et al., *J. Biol. Chem.*, 260: 7609-7613 (1985). The last copy of the ubiquitin sequence in the polyubiquitin gene is usually followed by one amino acid extension after the unique Arg-Gly-Gly terminus. Ozkaynak et al., supra.

Another discovery regarding cleavage of ubiquitin-protein conjugates revealed that when a chimeric gene encoding a ubiquitin-beta-galactosidase fusion protein was expressed in yeast, ubiquitin was cleaved from the fusion protein, yielding a deubiquitinated beta-galactosidase. This endoproteolytic cleavage was found to take place regardless of the nature of the amino acid residue of beta-gal at the ubiquitin-beta-gal junction, with one exception. Bachmain et al., *Science*, 234: 179-186 (1986). It was also found that different residues could be exposed at the amino-termini of the otherwise identical beta-gal proteins. These authors suggested that the same protease, as of then uncharacterized biochemically, was responsible both for the conversion of polyubiquitin into mature ubiquitin and for the deubiquitination of the nascent ubiquitin-beta-gal protein.

Different investigators detected a proteolytic activity that converted the polyubiquitin to ubiquitin when a coupled in vitro transcription/translation system was employed. Agell et al., *J. Cell Biol.*, 105: (4 pt 2), 82a (1987) and Agell et al., *Proc. Natl. Acad. Sci.*, U.S.A., 85: 3693–3697 (1988). The polyubiquitin processing activity was partially inhibited by ubiquitin aldehyde, a known inhibitor of ubiquitin hydrolase. A purified preparation of this proteolytic activity was found to be inactive, with further purification of the putative protease then reported to be in progress.

At the American Chemical Society meeting on Sep. 26, 1988, Chiron Corp. disclosed that fusion of a gene that has proven difficult to express directly to a synthetic gene for yeast ubiquitin has allowed high-level intracellular production of the desired protein as a mature polypeptide, cleaved in vivo by an endogenous yeast protease. See 1988 ACS Abstract Book, Abs. No. 34, P. J. Barr et al., "Production of Recombinant DNA Derived Pharmaceuticals in the Yeast Saccharomyces cerevisiae."

Regarding the purification of substances using an irreversible step such as cleavage, it was reported that fragments of proteins can be separated by charge or size in one dimension and then a reagent used to alter the protein fragments irreversibly for visualization in a second dimension. The object of this work was to obtain amino acid sequence from the protein. Hartley et al., *Biochem. J.*, 80: 36 (1961).

In addition, it is know to recover and purify a protein from its fusion product with an "identification" peptide. EP 150,126 published Jul. 31, 1985, equivalent to U.S. Pat. No. 4,703,004. In this process a hybrid polypeptide is synthesized with the identification peptide fused to a desired functional protein at the C-terminus of the indemnification peptide. The linking portion of the identification peptide is cleaved at a specific amino acid residue adjacent to the functional protein by using a sequence-specific proteolytic enzyme or chemical agent. The hybrid polypeptide is purified by affinity chromatography using an immobilized ligand specific to the antigenic portion of the identification peptide. The protein is then cleaved from the isolated hybrid polypeptide with an appropriate proteolytic agent to release the mature functional protein.

Recovery of a product from its fusion using an identification peptide linker or antibody is also disclosed. EP 35,384 published Sep. 9, 1981, and U.S. Pat. No. 4,732,852, issued Mar. 22, 1988. Moreover, recombinant production of polypeptides as fusion products with a charged amino acid polymer, separating the fusion product from contaminants based on the properties of the polymer, and cleaving the polymer from the fusion product using an exopeptidase has been reported. U.S. Pat. No. 4,532,207, issued Jul. 30, 1985.

The major problem associated with cleaving fusion proteins produced by recombinant means has been the lack of specific cleaving agents to remove the fusion protein moiety from the product protein in an exact and consistent manner. Chemical agents such as cyanogen bromide or hydroxylamine, or specific proteases such as Factor Xa or collagenase, that are used generally to achieve cleavage typically are only commercially practical in a limited number of protein fusion cleavages.

For example, if the specific amino acid that is required for the cleavage of a fusion protein (such as methionine for cyanogen bromide) is present internally in the amino acid sequence of the desired protein product, the product will be clipped internally as well as cleaved from the fused polypeptide. For this reason and other reasons, the cleaving agents are generally specific only for one protein product. In addition, the cleavage itself may leave extra amino acid residues on the product protein. Furthermore, almost all of the cleaving agents require extra recovery steps to purify the more complex mixture that is generated after cleavage.

Accordingly, it is an object of the present invention to provide a ubiquitin hydrolase that is purified to a sufficient degree that it can be sequenced.

It is another object to provide quantities of a ubiquitin hydrolase useful for commercial purposed by using recombinant means to produce the hydrolase, free of source proteins.

It is still another object to provide a procedure for obtaining a heretofore unidentified yeast ubiquitin hydrolase.

It is another object to provide a method for producing and purifying mature polypeptides, the method being characterized by removing the fusion protein moiety from the product moiety specifically and efficiently, by reducing the number and complexity of fusion recovery steps, and by obtaining precise and reproducible cleavage of the product free of extra unwanted terminal amino acid residues.

These and other objects will be obvious to those of ordinary skill in the art.

SUMMARY OF THE INVENTION

In one aspect of the invention herein, these objects are achieved by a composition comprising a ubiquitin hydrolase in a purity of at least 70% homogeneity based on the weight of the total protein in the composition.

In another aspect, the invention herein provides a process for purifying ubiquitin hydrolase comprising:
  (a) homogenizing a eukaryotic cell fermentation paste and recovering the portion from the homogenate containing ubiquitin-hydrolase activity;
  (b) salting out from the recovered hydrolase-containing portion of step (a) a precipitate containing ubiquitin-hydrolase activity;
  (c) contacting a solution of the precipitate with an ion exchange resin and recovering the ubiquitin-hydrolase-active fraction;
  (d) contacting a ubiquitin hydrolase-active fraction with a hydrophobic affinity resin and recovering the ubiquitin-hydrolase-active fraction adsorbed to the resin;
  (e) contacting a ubiquitin hydrolase-active fraction with an adsorption chromatography resin and recovering the ubiquitin-hydrolase-active fraction adsorbed to the resin; and
  (f) contacting a ubiquitin-hydrolase-active fraction with an ion exchange resin and recovering the hydrolase-active fraction.

In yet another aspect, the invention provides an isolated nucleic acid sequence comprising a sequence that encodes a ubiquitin hydrolase or fragments or variants thereof, an expression vector comprising this nucleic acid sequence operably linked to control sequences recognized by a host transformed by the vector, and host cells transformed by such a vector. The nucleic acid is preferably DNA, but can also be RNA or an RNA vector (retrovirus).

In a more specific aspect, the invention provides an isolated DNA sequence comprising a sequence that hybridizes under stringent conditions to the DNA sequence of FIG. 5 and that contains at least about ten nucleotides. Preferably the DNA sequence contains at least about twenty nucleotides, more preferably about thirty nucleotides, and most preferably, about 40 nucleotides.

In yet another embodiment, the invention provides an isolated DNA sequence comprising a DNA sequence encoding an enzyme having an amino acid sequence sufficiently duplicative of that of a ubiquitin hydrolase to allow it to hydrolyze a ubiquitin-polypeptide conjugate at the amide bond linking the ubiquitin and polypeptide, thereby yielding intact polypeptide with an unconjugated, mature N-terminus. The invention also provides for expression vectors containing such DNA sequence operably linked to appropriate control sequences, and hosts such as *E. coli* transformed with such vectors.

In a further aspect, the invention sets forth a method for in vitro cleavage of ubiquitin-polypeptide conjugates comprising:
(a) providing a ubiquitin-polypeptide conjugate in a composition comprising contaminant products of recombinant host cell culture, wherein the polypeptide is conjugated to the C-terminus of the ubiquitin and wherein the polypeptide contains any amino acid except proline at its N-terminus;
(b) contacting the composition with a reagent having specific affinity for ubiquitin so that the conjugate is adsorbed on the reagent, separating the reagent and its adsorbed conjugate from the rest of the composition, and recovering the conjugate from the reagent;
(c) contacting the recovered conjugate with ubiquitin hydrolase whereby the conjugate is hydrolyzed to ubiquitin and mature polypeptide and the ubiquitin hydrolase is immobilized; and
(d) contacting the material obtained from step (c) with a reagent having specific affinity for ubiquitin so that any residual conjugate and free ubiquitin are adsorbed on the reagent, and recovering the polypeptide free from the reagent and the materials adsorbed thereon.

In still another aspect, the invention is directed to a method for in vitro cleavage of ubiquitin-polypeptide conjugates comprising:
(a) providing a ubiquitin-polypeptide conjugate in a composition comprising contaminant products of recombinant host cell culture, wherein the polypeptide is conjugated to the C-terminus of the ubiquitin and wherein the polypeptide contains any amino acid except proline at its N-terminus;
(b) contacting the composition with a reagent having specific affinity for ubiquitin so that the conjugate is adsorbed on the reagent and separating the reagent and its adsorbed conjugate from the rest of the composition;
(d) contacting the reagent on which is adsorbed the conjugate with ubiquitin hydrolase;
(e) separating the hydrolase and polypeptide from the reagent; and
(f) separating the polypeptide from the hydrolase.

In still another aspect, the invention provides a method for in vivo cleavage of ubiquitin-polypeptide conjugates comprising:

(a) culturing prokaryotic host cells that have DNA encoding a ubiquitin hydrolase integrated into their chromosomes and are transformed with an expression vector comprising a nucleotide sequence encoding a ubiquitin-polypeptide conjugate wherein the polypeptide is conjugated to the C-terminus of the ubiquitin and wherein the polypeptide contains any amino acid except proline at its N-terminus such that the conjugate is expressed; and
(b) recovering from the cultured cells the polypeptide free from the ubiquitin to which it was conjugated.

In yet another aspect, the invention provides prokaryotic host cells having DNA encoding a ubiquitin hydrolase integrated into their chromosomes. Most preferred of these are those host cells that are also transformed with an expression vector comprising a nucleotide sequence encoding a ubiquitin-polypeptide conjugate wherein the polypeptide is conjugated to the C-terminus of the ubiquitin and wherein the polypeptide contains any amino acid except proline at its N-terminus.

This invention also relates to an isolated yeast ubiquitin hydrolase encoded by DNA that does not hybridize to the DNA sequence that hybridizes under stringent conditions to the DNA sequence of FIG. 5 and that contains at least about ten nucleotides, preferably at least about 20, more preferably at least about 30, and most preferably at least about 40 nucleotides. Similarly, the invention provides an isolated nucleic acid sequence encoding a ubiquitin hydrolase comprising a nucleic acid sequence that does not hybridize to the above-identified DNA sequence. In addition, the invention furnishes an expression vector comprising this nucleic acid sequence operably linked to control sequences recognized by a host transformed by the vector. Finally, the invention provides a host cell transformed with this expression vector.

In further aspects, the invention provides an enzyme composition comprising the ubiquitin hydrolase of this invention in a buffer and a kit comprising a ubiquitin hydrolase as one component and immobilized anti-ubiquitin antibody as a second component.

The present invention makes it possible to produce a ubiquitin hydrolase or derivatives thereof by recombinant techniques, as well as to provide products and methods related to such production. In addition, this invention enables a simplified and effective method for recovering mature proteins and polypeptides from their fusion with another protein. Further, the invention allows variant polypeptides and proteins to be expressed without concern about secretion or cleavage in undesired positions.

The in vivo cleavage technique herein permits the intracellular production of polypeptides from prokaryotes that are ordinarily unstable in the cell or that are not desired to be secreted, such as human growth hormone having no N-terminal methionine and γ-interferon. In the former case, the N-terminal methionine need not be present during production nor later removed after the protein is recovered form the medium.

BRIEF DESCRIPTION OF THE DRAWINGS

FIG. 1a (parts 1 and 2) depicts the sequence of a synthetic gene extending from XbaI to HindIII sites encoding a ubiquitin fusion polypeptide wherein the polypeptide is the human (h2) relaxin B chain of 32 amino acids (missing the N-terminal amino acid) linked at its N-terminus to a hexapeptide. The hexapeptide is in turn linked at its N-terminus to the C-terminus of ubiquitin. The six amino acids do not code for any naturally occurring sequence. FIG. 1b (parts 1 and 2) depicts the sequence of a synthetic gene extending from DraIII to HindIII sites encoding a ubiquitin fusion polypeptide wherein the polypeptide is the 33-amino-acid human (H2) relaxin B chain.

FIG. 3 (parts a-d) depicts the nucleotide and predicted amino acid sequence of a yeast ubiquitin hydrolase (designated herein as YUH-1). Predicted amino acids of the protein are shown below the DNA sequence and are numbered from the first residue of the proposed N-terminus of the protein sequence. The figure also indicates the amino acid sequence of the polypeptide used to derive Probe 1 for screening a yeast genomic library to obtain a clone encoding a yeast ubiquitin hydrolase.

FIG. 4 depicts the orientation of the BamHI-SalI fragment in M13mp18 and M13mp19 for sequencing the gene coding for the yeast ubiquitin hydrolase.

FIG. 5 (parts a-d) depicts the nucleotide sequence and predicted amino acid sequence of the yeast ubiquitin hydrolase YUH-1 as shown in FIG. 3 and its flanking region from HindIII to BamHI. The location of the three sequenced peptides (numbered 14, 8 and 17) is indicated with stars. The 53-mer probe sequence is shown below the correct DNA sequence. Mismatches are indicated as lower case letters. The probe is 87% identical with the correct DNA sequence.

FIG. 10 shows the final steps in the assembly of the pT7-12ST2TPA-1 vector bearing the STII-tPA gene under the transcriptional control of the phi 10 promoter.

FIG. 18 depicts Southern blots of diploid and haploid yeast that are transformed with the SalI-EcoRI fragment containing the YUH::URA3 gene interruption.

DETAILED DESCRIPTION OF THE PREFERRED EMBODIMENTS

A. Definitions

Figure 1C:
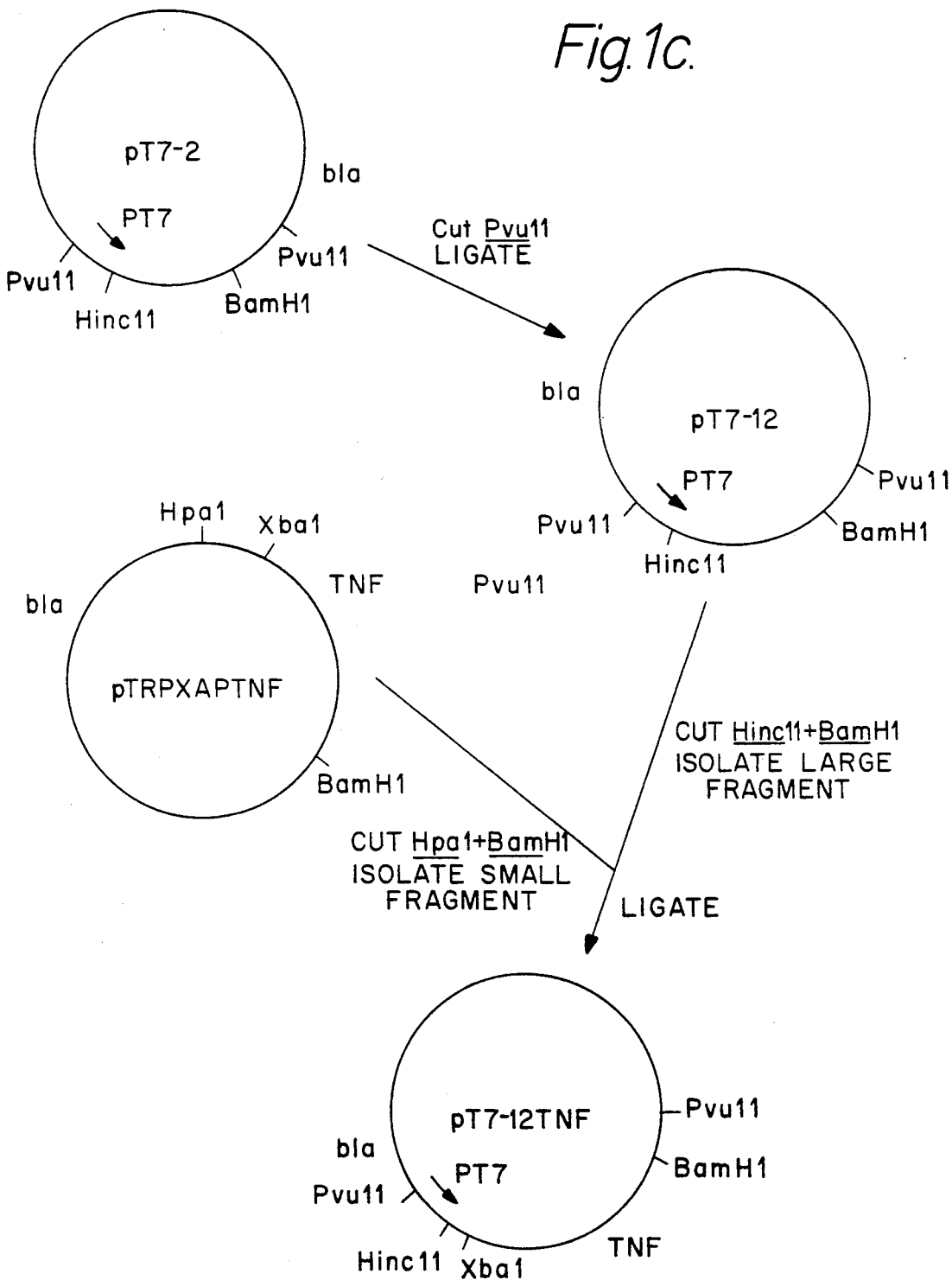
FIG. 1c depicts the construction of pT7-12TNF, an intermediate plasmid providing the phi 10 promoter recognized by T7 polymerase ($P_{T7}$).

The term "ubiquitin hydrolase" as used herein refers to an enzyme, whether having the sequence of the native molecule or being a derivative or amino acid sequence variant thereof, that possesses ubiquitin hydrolase biological activity. Biological activity is one or both of (a) the capability to hydrolyze a ubiquitin-polypeptide conjugate at the amide bond linking the ubiquitin and polypeptide, thereby yielding intact polypeptide with an unconjugated, mature N-terminus, or (b) the ability to cross-react with an antibody that binds to the FIG. 5 polypeptide. There are at least two naturally occurring yeast ubiquitin hydrolase proteins. The full-length version of one of these, which corresponds to the one with the amino acid sequence of FIG. 5, has a molecular weight of about 29,000 daltons on a reducing SDS-PAGE gel. The amino acid sequence from the cloned gene revealed the molecular weight as 26,000 daltons. Generally, the enzyme is from eukaryotes.

Derivatives and amino acid sequence variants are defined as molecules in which the amino acid sequence, or other feature of a native ubiquitin hydrolase, has been modified covalently or noncovalently. Amino acid sequence yeast variants include not only alleles of the FIG. 5 sequence, but also predetermined mutations thereof. Generally, amino acid sequence variants have an amino acid sequence with at least about 80% homology, and more typically at least about 90% homology, to that of a native ubiquitin hydrolase, e.g., the one shown in FIG. 5. Henceforth, the term "ubiquitin hydrolase" shall mean any one of the native sequences or a variant form unless otherwise appropriate.

Thus, included within the scope of the present invention is a yeast ubiquitin hydrolase having the amino acid sequence as set forth in FIG. 5 (YUH-1), analogous ubiquitin hydrolase proteins from other microbial, vertebrate, or invertebrate eukaryatic species such as inset, human, bovine, equine, porcine, ovine, canine, murine, feline ubiquitin hydrolase, and the like, a yeast ubiquitin hydrolase (designated herein as YUH-2) encoded by DNA that does not hybridize with the nucleotide sequence shown in FIG. 5, even under low stringency, and biologically active amino acid sequence variants of these ubiquitin hydrolases, including alleles and in vitro-generated covalent derivatives of ubiquitin hydrolase proteins that demonstrate the enzyme's activity.

The term "polypeptide" refers to a product with more than one peptide bond, including a dipeptide, tripeptide, and proteins of any size, or a mutant or fragment thereof.

The term "ubiquitin-polypeptide conjugate" refers to conjugates of ubiquitin (where the 76th amino acid is glycine) to the polypeptide defined above at the C-terminus of the ubiquitin, where the polypeptide has as its N-terminal residue any amino acid except proline.

The expression "at least 70% homogeneity" refers to the weight of a ubiquitin hydrolase in total protein, as determined by a comparative visual inspection of a silver-stained SDS-PAGE gel for relative intensities of the bands.

The term "buffer" refers to a buffer that is characterized by its ability to stabilize the enzyme herein at a suitable pH range, of generally around 3 to 10, more preferably 4 to 8.

B. Modes of Carrying Out the Invention

1. Purification of A Ubiquitin Hydrolase

The steps involved in purifying a ubiquitin hydrolase of this invention are enumerated below. This method is useful for purifying a ubiquitin hydrolase from recombinant or non-recombinant cells.

Eukaryotic cells, preferably yeast such as *Saccharomyces cerevisiae* or another yeast strain, are fermented, as by using standard conditions known in the art, and a fermentation paste is obtained. The paste is homogenized and the portion from the homogenate containing ubiquitin-hydrolase activity is recovered, preferably by centrifugation. The activity may be assayed as described in the examples.

A precipitate containing ubiquitin-hydrolase activity is salted out from the recovered hydrolase-containing portion. Preferably the salting out is done using ammonium sulfate fractionation, but any salt suitable for this purpose may be employed.

A solution of the precipitate is contacted with an ion exchange resin and the ubiquitin-hydrolase-active fraction is recovered. Preferably the ion exchange resin is a DEAE chromatography column and the fraction is adsorbed to the column and recovered from the column.

The ubiquitin hydrolase-active fraction is contacted with a hydrophobic affinity resin, such as a phenyl, octyl, or cetyl sepharose chromatographic column, and the ubiquitin-hydrolase-active fraction adsorbed to the resin is obtained and recovered. The fraction recovered from this step is preferably dialyzed against a buffer before the next step is performed.

The ubiquitin hydrolase-active fraction is contacted with an adsorption chromatography resin, such as a hydroxyapatite or silica column, and the ubiquitin-hydrolase-active fraction adsorbed to the resin is recovered. The fraction recovered from this step is preferably dialyzed against a buffer before the next step is performed. Most preferably, the adsorption chromatography is done by hydroxyapatite column chromatography and the active fraction is adsorbed to the column and recovered therefrom.

The ubiquitin-hydrolase-active fraction is again contacted with an ion exchange resin, such as a DEAE chromatography column, and the hydrolase-active fraction is adsorbed to the column and recovered therefrom.

The ubiquitin hydrolase is then generally isolated from the ubiquitin-hydrolase-active fraction in a purity of at least 70% by the weight of the total protein. Liquid chromatography may be employed in this isolation procedure.

2. Modifications of Ubiquitin Hydrolases

Derivatives and amino acid sequence variants of ubiquitin hydrolases are useful for their enzymatic activity, as is set forth elsewhere herein, as well as for their ability to bind to anti-ubiquitin hydrolase antibodies. The derivatives and variants possessing the latter characteristic are useful in purifying antibodies or, when labeled, as reagents in immunoassays for ubiquitin hydrolase, whether or not such derivatives and variants retain their enzymatic activity.

a. Covalent modification

Covalent modifications of a ubiquitin hydrolase molecule are included within the scope of this invention. Variant ubiquitin hydrolase fragments having up to about 100 residues may be conveniently prepared by in vitro synthesis. Such modifications may be introduced into the molecule by reacting targeted amino acid residues of the purified or crude protein with an organic derivatizing agent that is capable of reacting with selected side chains or terminal residues. The resulting covalent derivatives are useful in programs directed at identifying residues important for biological activity.

Cysteinyl residues most commonly are reacted with $\alpha$-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, $\alpha$-bromo-$\beta$-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5–7.0 because this agent is relatively specific for the histidyl side chain. Parabromophenacyl bromide also is useful; the reaction is preferably performed in 0.1 M sodium cacodylate at pH 6.0.

Lysinyl and amino terminal residues are reacted with succinic or other carboxylic acid anhydrides. Derivatization with these agents has the effect of reversing the charge of the lysinyl residues. Other suitable reagents for derivatizing $\alpha$-amino-containing residues include imidoesters such as methyl picolinimidate; pyridoxal phosphate; pyridoxal; chloroborohydride; trinitrobenzenesulfonic acid; 0-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high $pK_a$ of the guanidine functional group. Furthermore, these reagents may react with the groups of lysine as well as the arginine epsilon-amino group.

The specific modification of tyrosyl residues per se has been studies extensively, with particular interest in introducing spectral labels into tyrosyl residues by reaction with aromatic diazonium compounds or tetranitromethane. Most commonly, N-acetylimidizol and tetranitromethane are used to form -acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'-N-C-N-R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the ubiquitin hydrolase to a water-insoluble support matrix or surface for use in the method for cleaving ubiquitin fusion polypeptides to release and recover the cleaved polypeptide. Commonly used crosslinking agents include, e.g., 1,1-bis(diazoacetyl)-b 2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, *Proteins: Structure and Molecular Properties*, W. H. Freeman & Co., San Francisco, pp. 79-86 [1983]), acetylation of the N-terminal amine, and, in some instances, amidation of the C-terminal carboxyl group.

b. Mutation(s) in the DNA

Amino acid sequence variants of a ubiquitin hydrolase can also be prepared by mutations in the DNA. Such variants include, for example, deletions from, or insertions or substitutions of, residues within the amino acid sequence shown in FIG. 3. Any combination of deletion, insertion, and substitution may also be made to arrive at the final construct, provided that the final construct possesses the desired activity. Obviously, the mutations that will be made in the DNA encoding the variant must not place the sequence out of reading frame and preferably will not create complementary regions that could produce secondary mRNA structure (see EP 75,444A).

At the genetic level, these variants ordinarily are prepared by site-directed mutagenesis of nucleotides in the DNA encoding the ubiquitin hydrolase, thereby producing DNA encoding the variant, and thereafter expressing the DNA in recombinant cell culture. The variants typically exhibit the same qualitative biological activity as the naturally occurring analog.

While the site for introducing an amino acid sequence variation is predetermined, the mutation per se need not be predetermined. For example, to optimize the performance of a mutation at a given site, random mutagenesis may be conducted at the target codon or region and the expressed ubiquitin hydrolase variants screened for the optimal combination of desired activity. Techniques for making substitution mutations at predetermined sites in DNA having a known sequence are well known, for example, site-specific mutagenesis.

Preparation of ubiquitin hydrolase variants in accordance herewith is preferably achieved by site-specific mutagenesis of DNA that encodes an earlier prepared variant or a nonvariant version of the protein. Site-specific mutagenesis allows the production of ubiquitin hydrolase variants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art, as exemplified by publications such as Adelman et al., *DNA*, 2: 183 (1983), the disclosure of which is incorporated herein by reference.

As will be appreciated, the site-specific mutagenesis technique typically employs a phage vector that exists in both a single-stranded and double-stranded form. Typical vectors useful in site-directed mutagenesis include vectors such as the M13 phage, for example, as disclosed by Messing et al., *Third Cleveland Symposium on Macromolecules and Recombinant DNA*, Editor A. Walton, Elsevier, Amsterdam (1981), the disclosure of which is incorporated herein by reference. These phage are readily commercially available and their use is generally well know to those skilled in the art. Alternatively, plasmid vectors that contain a single-stranded phage origin of replication (Veira et al., *Meth. Enzymol.*, 153: 3 [1987]) may be employed to obtain single-stranded DNA.

In general, site-directed mutagenesis in accordance herewith is performed by first obtaining a single-stranded vector that includes within its sequence a DNA sequence that encodes the relevant protein. An oligonucleotide primer bearing the desired mutated sequence is prepared, generally synthetically, for example, by the method of Crea et al., *Proc. Natl. Acad. Sci.* (U.S.A.), 75: 5765 (1978). This primer is then annealed with the single-stranded protein-sequence-containing vector, and subjected to DNA-polymerizing enzymes such as *E. coli* polymerase I Klenow fragment, to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected that include recombinant vectors bearing the mutated sequence arrangement.

After such a clone is selected, the mutated protein region may be removed and placed in an appropriate vector for protein production, generally an expression vector of the type that may be employed for transformation of an appropriate host.

c. Types of Mutations

Amino acid sequence deletions generally range from about 1 to 30 residues, more preferably 1 to 10 residues, and typically are contiguous.

Amino acid sequence insertions include amino- and/or carboxyl-terminal fusions of from one residue to polypeptides of essentially unrestricted length, as well as intrasequence insertions of single or multiple amino acid residues. Intrasequence insertions (i.e., insertions within the mature ubiquitin hydrolase sequence) may range generally from about 1 to 10 residues, more preferably 1 to 5. An example of a terminal insertion includes a fusion of a signal sequence, whether heterologous or homologous to the host cell, to the N-terminus of the ubiquitin hydrolase to facilitate the secretion of mature ubiquitin hydrolase from recombinant hosts.

The third group of variants are those in which at least one amino acid residue in the ubiquitin hydrolase molecule, and preferably only one, has been removed and a different residue inserted in its place. Such substitutions preferably are made in accordance with the following Table 1 when it is desired to modulate finely the characteristics of a ubiquitin hydrolase molecule.

TABLE 1

| Original Residue | Exemplary Substitutions |
| --- | --- |
| Ala | gly; ser |
| Arg | lys |
| Asn | gln; his |
| Asp | glu |
| Cys | ser |
| Gln | asn |
| Glu | asp |
| Gly | ala; pro |
| His | asn; gln |
| Ile | leu; val |
| Leu | ile; val |
| Lys | arg; gln; glu |
| Met | leu; tyr; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 1, i.e., selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to produce the greatest changes in ubiquitin hydrolase properties will be those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

Most deletions and insertions, and substitutions in particular, are not expected to produce radical changes in the characteristics of the ubiquitin hydrolase molecule. However, when it is difficult to predict the exact effect of the substitution, deletion, or insertion in advance of doing so, one skilled in the art will appreciate that the effect will be evaluated by routine screening assays. For example, a variant typically is made by site-specific mutagenesis of the native ubiquitin hydrolase-encoding nucleic acid, expression of the variant nucleic acid in recombinant cell culture, and, optionally, purification from the cell culture, for example, by immunoaffinity adsorption on a rabbit polyclonal anti-ubiquitin hydrolase column (to absorb the variant by binding it to at least one remaining immune epitope).

The activity of the cell lysate or purified ubiquitin hydrolase variant is then screened in a suitable screening assay for the desired characteristic. For example, a change in the immunological character of the ubiquitin hydrolase, such as affinity for a given antibody, is measured by a competitive-type immunoassay. Changes in immunomodulator activity are measured by the appropriate assay. Modifications of such protein properties as redox or thermal stability, hydrophobicity, susceptibility to proteolytic degradation, or the tendency to aggregate with carriers or into multimers are assayed by methods well known to the ordinarily skilled artisan.

3. Recombinant Expression

The ubiquitin hydrolase molecule desired may be prepared by any technique, including recombinant methods. Likewise, an isolated DNA is understood herein to mean chemically synthesized DNA, cDNA, chromosomal, or extrachromosomal DNA with or without the 3'- and/or 5'-flanking regions. Preferably, the desired ubiquitin hydrolase herein is made by synthesis in recombinant cell cultural.

For such synthesis, it is first necessary to secure nucleic acid that encodes a ubiquitin hydrolase. DNA encoding a ubiquitin hydrolase molecule may be obtained from yeast or other sources than yeast by (a) obtaining a DNA library from the appropriate strain, (b) conducting hybridization analysis with labeled DNA encoding the ubiquitin hydrolase or fragments thereof (up to or more than 100 base pairs in length) to detect clones in the library containing homologous sequences, and (c) analyzing the clones by restriction enzyme analysis and nucleic acid sequencing to identify full-length clones. DNA that is capable of hybridizing to a ubiquitin-hydrolase-encoding DNA under stringent conditions is useful for identifying DNA encoding the particular ubiquitin hydrolase desired. Stringent conditions are defined further below. If full-length clones are not present in a cDNA library, then appropriate fragments may be recovered from the various clones using the nucleic acid sequence information disclosed herein for the first time and ligated at restriction sites common to the clones to assemble a full-length clone encoding the ubiquitin hydrolase. Alternatively, genomic libraries will provide the desired DNA. The sequence of the yeast DNA encoding one type of yeast ubiquitin hydrolase that was ultimately determined is shown in FIG. 5.

Once this DNA has been identified and isolated from the library it is ligated into a replicable vector for further cloning or for expression.

In one example of a recombinant expression system a ubiquitin hydrolase is expressed in prokaryotes by transforming with an expression vector comprising DNA encoding the ubiquitin-hydrolase. It is preferable to transform host cells capable of accomplishing such processing so as to obtain the hydrolase in the culture medium or periplasm of the host cell.

a. Useful Host Cells and Vectors

The vectors and methods disclosed herein are suitable for use in host cells over a wide range of prokaryotic and eukaryotic organisms.

In general, of course, prokaryotes are preferred for the initial cloning of DNA sequences and construction of the vectors useful in the invention. For example, *E. coli* K12 strain MM 294 (ATCC No. 31,446) is particularly useful. Other microbial strains that may be used include *E. coli* strains such as *E. coli* B and *E. coli* X1776 (ATCC No. 31,537). These examples are, of course, intended to be illustrative rather than limiting.

Prokaryotes may also be used for expression. The aforementioned strains, as well as *E. coli* strains W3110 (F-, lambda-, prototrophic, ATCC No. 27,325), K5772 (ATCC No. 53,635), and SR101, bacilli such as *Bacillus subtilis*, and other enterobacteriaceae such as *Salmonella typhimurium* or *Serratia marcesans*, and various pseudomonas species, may be used.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. coli* is typically transformed using pBR322, a plasmid derived from a *E. coli* species (see, e.g., Bolivar et al., *Gene*, 2: 95 [1977]). pBR322 contains genes for ampicillin and tetracycline resistance and thus provides easy means for identifying transformed cells. The pBR322 plasmid, or other microbial plasmid or phage, must also contain, or be modified to contain, promoters that can be used by the microbial organism for expression of its own proteins.

Those promoters most commonly used in recombinant DNA construction include the β-lactamase (penicillinase) and lactose promoter systems (Change et al., *Nature*, 375: 615 [1978]; Itakura et al., *Science*, 198: 1056 [1977]; Goeddel et al., *Nature*, 281: 544 [1979]) and a tryptophan (trp) promoter system (Goeddel et al., *Nucleic Acids Res.*, 8: 4057 [1980]; EPO Appl. Publ. No. 0036,776). While these are the most commonly used, other microbial promoters have been discovered and utilized, and details concerning their nucleotide sequences have been published, enabling a skill worker to ligate them functionally with plasmid vectors (see, e.g., Siebenlist et al., *Cell*, 20: 269 [1980]).

In addition to prokaryotes, eukaryotic microbes, such as yeast cultures, may also be used. *Saccharomyces cerevisiae*, or common baker's yeast, is the most commonly used among eukaryotic microorganisms, although a number of other strains are commonly available. For expression in *Saccharomyces*, the plasmid YRp7, for example (Stinchcomb et al., *Nature*, 282: 39 [1979]; Kingsman et al., *Gene*, 7: 141 [1979]; tschemper et al., *Gene*, 10: 157 [1980]), is commonly used. This plasmid already contains the trpl gene that provides a selection marker for a mutant strain of yeast lacking the ability to grow in tryptophan, for example, ATCC No. 44,076 or PEP4-1 (Jones, *Genetics*, 85: 12 [1977]). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.*, 255: 2073 [1980]) or other glycolytic enzymes (Hess et al., *J. Adv. Enzyme Reg.*, 7: 149 [1968]; Holland et al., *Biochemistry*, 17: 4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions, are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and W138, BHK, COS-7, 293, and MDCK cell lines. Expression vectors for such cells ordinarily include (if necessary) an origin of replications, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment that also contains the SV40 viral origin of replication (Fiers et al., *Nature*, 273: 113 [1978]). Smaller or larger SV40 fragments may also be used, provided there is included the approximately 250-bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Satisfactory amounts of protein are produced by cell cultures; however, refinements, using a secondary coding sequence, serve to enhance production levels even further. One secondary coding sequence comprises dihydrofolate reductase (DHFR) that is affected by a externally controlled parameter, such as methotrexate (MTX), thus permitting control of expression by control of the methotrexate concentration.

In selecting a preferred host cell for transfection by the vectors of the invention that comprises DNA sequences encoding both ubiquitin hydrolase and DHFR protein, it is appropriate to select the host according to the type of DHFR protein employed. If wild-type DHFR protein is employed, it is preferable to select a host cell that is deficient in DHFR, thus permitting the use of the DHFR coding sequence as a marker for successful transfection in selective medium that lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci.* (U.S.A.) 77: 4216 (1980).

On the other hand, if DHFR protein with low binding affinity for MTX is used as the controlling sequence, it is not necessary to use DHFR-deficient cells. Because the mutant DHFR is resistant to methotrexate, MTX-containing media can be used as a means of selection provided that the host cells are themselves methotrexate sensitive. Most eukaryotic cells that are capable of absorbing MTX appear to be methotrexate sensitive. One such useful cell line is a CHO line, CHO-K1 (ATCC No. CCL 61).

b. Typical Methodology Employable

Construction of suitable vectors containing the desired coding and control sequences employs standard ligation techniques. Isolated plasmids or DNA fragments are cleaved, tailored, and religated in the form desired to prepare the plasmids required.

If blunt ends are required, the preparation may be treated for 15 minutes at 15° C. with 10 units of Polymerase I (Klenow), phenol-chloroform extracted, and ethanol precipitated.

Size separation of the cleaved fragments may be performed using 6 percent polyacrylamide gel described by Goeddel et al., *Nucleic Acids Res.*, 8: 4057 (1980).

For analysis to confirm correct sequences in plasmids constructed, the ligation mixtures are typically used to transform *E. coli* K12 strain 294 (ATCC 31,446) or other suitable *E. coli* strains, and successful transformants selected by ampicillin or tetracycline resistance where appropriate. Plasmids from the transformants are prepared and analyzed by restriction mapping and/or DNA sequencing by the method of Messing et al., *Nucleic Acids Res.*, 9: 309 (1981) or by the method of Maxam et al., *Methods of Enzymology*, 65: 499 (1980).

After introduction of the DNA into the mammalian cell host and selection in medium for stable transfectants, amplification of DHFR-protein-coding sequences is effected by growing host cell cultures in the presence of approximately 20,000-500,000 nM concentration of methotrexate, a competitive inhibitor of DHFR activity. The effective range of concentration is highly dependent, of course, upon the nature of the DHFR gene and the characteristics of the host. Clearly, generally defined upper and lower limits cannot be ascertained. Suitable concentrations of other folic acid analogs or other compounds that inhibit DHFR could also be used. MTX itself is, however, convenient, readily available, and effective.

Other techniques employable are described in a section just prior to the examples.

4. Process for Cleaving Fusion Polypeptides in vitro

The ubiquitin hydrolase molecules herein are particularly useful in a process for readily processing in vitro a fusion polypeptide between ubiquitin and any polypeptide product desired. Ubiquitin fusion polypeptides are expressed generally by a chimeric gene construct comprising a ubiquitin gene ligated at its 3' end to the 5' end of a gene coding for the desired polypeptide. The ubiquitin gene is obtained from a natural source and cloned into an appropriate vector, as described in WO 88/02406, supra, the disclosure of which is incorporated herein by reference, or it is synthesized chemically, using, e.g., the method described by Ecker et al., *J. Biol. Chem.*, 262:3524-3527 (1987) and Ecker et al., *J. Biol. Chem.*, 262: 14213-14221 (1987), the disclosure of which are incorporated by reference. The fusion in turn optionally contains an N-terminal signal sequence to facilitate secretion of the fusion polypeptide.

The codon for the N-terminal amino acid of the desired polypeptide is located directly adjacent to the 3' end of the ubiquitin gene or is separated by any number of nucleotide triplets (typically one, two, or three triplets) that need not encode any particular sequence but which keep the gene encoding the desired polypeptide in the correct reading frame.

The desired polypeptide may be any polypeptide, including, but not limited to, mammalian polypeptides, such as, e.g., a growth hormone, including human growth hormone, des-N-methionyl human growth hormone, and bovine growth hormone; insulin A-chain, insulin B-chain; proinsulin; factor VIII; a plasminogen activator, such as urokinase or human tissue-type plasminogen activator (t-PA); tumor necrosis factor-alpha and -beta; enkephalinase; a serum albumin such as human serum albumin; mullerian-inhibiting substance; relaxin A-chain; relaxin B-chain; proprelaxin; mouse gonadotropin-associated peptide; a microbial protein, such as beta-lactamase; DNase; tissue factor protein; inhibin; activin; nerve growth factor such as NGF-$\beta$; platelet-derived growth factor; fibroblast growth factor; transforming growth factor (TGF) such as TGF-alpha and TGF-beta; insulin-like growth factor-I and -II; insulin-like growth factor binding proteins; CD-4; erythropoietin; an interferon such as inteferon-alpha, -beta, and -gamma; colony stimulating factors (CSFs), e.g., M-CSF, GM-CSF, and G-CSF; interleukins (ILs), e.g., IL-1, IL-2, IL-3, IL-4, etc.; superoxide dismutase; decay accelerating factor; viral antigen such as, for example, a portion of the AIDS envelope; fragments of any of the above-listed polypeptides; and the like. In addition, one or more predetermined amino acid residues on the polypeptide may be substituted, inserted, or deleted, without adversely affecting the expression and/or ubiquitin hydrolase processing of the fusion.

Preferably, the polypeptide herein is relaxin or insulin A-chain or B-chain, proprelaxin, proinsulin, an interferon, an interleukin, a growth hormone, a nerve growth factor, a transforming growth factor, an insulin-like growth factor, or DNase. Most preferably, the polypeptide herein is relaxin or insulin A-chain or B-chain, prorelaxin, proinsulin, interferon-gamma, or des-N-methionyl human growth hormone. Also, preferably the polypeptide is a polypeptide heterologous to the host cell in which it is expressed, and is a human polypeptide.

The fusion is produced in a composition comprising contaminant products of recombinant cell culture and then cleaved so as to recover the desired polypeptide product. The polypeptide is conjugated to the C-terminus of the ubiquitin and contains any amino acid at its N-terminus. The host cell culture containing the fusion if grown in culture medium appropriate to the host and harvested by a method dependent on whether the fusion is secreted. In general, the cells are lysed and centrifuged to spin out the cellular debris and recover the fusion protein in the supernatant. The supernatant or secreted fusion material recovered from the periplasm, e.g., by osmotic shock, or from the extracellular medium is then contacted with a reagent having specific affinity for ubiquitin so that the conjugate is adsorbed on the reagent. This reagent may be any reagent, such as a cellular protein that interacts with the ubiquitin or an anti-ubiquitin antibody, preferably a monoclonal antibody. Most preferably, the separation takes place on a affinity chromatography column to which a monoclonal antibody against ubiquitin in bound.

In the next step, the reagent having specific affinity for ubiquitin and its adsorbed conjugate is separated from the rest of the host cell culture, and the conjugate is recovered from the reagent. If the adsorbed conjugate is on an affinity column, the conjugate adsorbed to the antibody is recovered by elution from the column using a pH gradient of 4-5.

In the following step, the recovered conjugate is contacted with a ubiquitin hydrolase, whereby the conjugate is hydrolyzed to ubiquitin and mature polypeptide and the hydrolase is immobilized. This may be accomplished by passing the eluted conjugate through a column to which the ubiquitin hydrolase is bound. Alternatively, the conjugate is contacted with the ubiquitin hydrolase and then an antibody against the hydrolase that is immobilized is used to separate the hydrolase from the conjugate.

The recovered material is then contacted with a reagent having specific affinity for ubiquitin so that any residual conjugate and free ubiquitin are adsorbed on the reagent, and the polypeptide is recovered free from the reagent and the materials adsorbed thereon. Again, this reagent may be a monoclonal antibody against ubiquitin, which may be bound to an affinity column.

For the success of this process, the host cell preferably produces no endogenous ubiquitin hydrolase that will interfere with the recovery process. This can be achieved either by using a prokaryotic host, which in general produces no ubiquitin hydrolase, or by employing deletion or transposon mutagenesis to rid the host cell, i.e., a eukaryotic host cell, of all genes that code for endogenous ubiquitin hydrolases. It may also be desirable to select host cells deficient in endogenous proteases that might degrade the fusion polypeptide if it is produced intracellularly, e.g., in a prokaryotic host.

In another method for recovering the cleaved polypeptide, after the host cell culture producing the conjugate is harvested as described above, the culture is contacted with the reagent having specific affinity for ubiquitin so that the conjugate is adsorbed on the reagent (the reagent being defined as described above). The reagent and its adsorbed conjugate are separated from the rest of the culture. Then the reagent on which is adsorbed the conjugate is contacted with the ubiquitin hydrolase. The hydrolase and polypeptide are separated from the reagent, and, in a final step, the polypeptide is separated from the hydrolase. The same preferred embodiments mentioned for the first process also apply to this process.

5. Antibodies to Ubiquitin

Antibodies to ubiquitin generally are raised in animals by multiple subcutaneous or intraperitoneal injections of ubiquitin and an adjuvant. It may be useful to conjugate the ubiquitin to a protein that is immunogenic in the species to be immunized, e.g., keyhole limpet hemocyanin, serum albumin, bovine thyroglobulin, or soybean trypsin inhibitor using a bifunctional or derivatizing agent, for example, mealeimidobenzoyl sulfosuccinimide ester (conjugation through cysteine residues), N-hydroxysuccinimide (through lysine residues), glutaraldehyde, succinic anhydride, $SOCl_2$ or $R^1N=C=NR$. Also, aggregating agents such as alum may be used to enhance the immune response.

Animals are immunized against the immunogenic conjugates or derivatives by combining 1 mg or 1 μg of conjugate (for rabbits or mice, respectively) with three volumes of Freund's complete adjuvant and injecting the solution intradermally at multiple sites. One month later the animals are boosted with 1/5 to 1/10 the original amount of conjugate in Freund's complete adjuvant by subcutaneous injection at multiple sites. Seven to 14 days later animals are bled and the serum is assayed for anti-ubiquitin titer. Animals are boosted until the titer plateaus. Preferably, the animal is boosted with the conjugate of the same ubiquitin polypeptide, but conjugated to a different protein and/or through a different crosslinking agent.

Monoclonal antibodies are prepared by recovering spleen cells from immunized animals and immortalizing the cells in conventional fashion, e.g., by fusion with myeloma cells or by Epstein-Barr virus transformation and screening for clones expressing the desired antibody. Monoclonal antibodies to ubiquitin are described, for example, in Smith and Fried. *Fed. Proc.*, 46(6): 2087 (1987), and polyclonal antisera are described by Redman et al., *J. Biol. Chem.*, 263: 4926-4931 (1988).

6. Process for Cleaving Fusion Polypeptides in vivo

Ubiquitin hydrolases are also particularly useful in a method for processing in vivo a fusion polypeptide between ubiquitin and any polypeptide product desired. The gene construct for the conjugate is as described in Section 4 above.

This gene construct is transformed into any prokaryotic host cells that have had integrated into their genome the gene coding for a ubiquitin hydrolase, preferably as a single copy in the chromosome. Such cells may be prepared by cloning a DNA construct having a promotor linked to the 5'end of a ubiquitin hydrolase gene into a lambda phage and integrating it into the appropriate strain. Preferably the host cells are *E. coli* cells, e.g., those having the characteristics of *E. coli* strain K5808, which was deposited in the American Type Culture Collection 12301 Parklawn Drive, Bethesda, Md., U.S.A. under ATCC Accession No. 53,832 on Nov. 30, 1988. This strain contains the YUH-1 gene construct driven by the trp promoter in a λgt11 phage integrated into the lambda attachment site between gal and bio of *E. coli* strain K5772.

Strain K5772 (ATCC No. 53,636) contains the T7 RNA polymerase gene inserted into the chromosomal lacZ operon that is thus inducible by addition of isopropylthiogalactoside (IPTG) to the media. The constitutive level of expression of T7 RNA polymerase depends on the untranslated domain located 5' to the polymerase structural gene. The T7 polymerase gene integrated in *E. coli* K5772 contains the following sequence (the complementary strand is not shown):

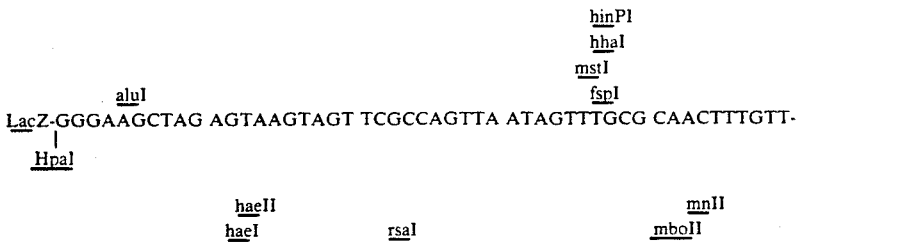

polymerase start.

The HpaI site is the first HpaI of the *E. coli* lacZ.

The resulting transformed host cells are cultured so as to express the ubiquitin-polypeptide conjugate. Culturing is preferably accomplished by inducing the promoter for the hydrolase gene. Thus, if trp is used as the promoter, the cells are cultured in minimal media without tryptophan. The induction results in efficient cleavage of ubiquitin-relaxin A-chain fusion in 20 minutes. As soon as the conjugate is expressed, it is cleaved by the ubiquitin hydrolase coded for in the genome.

7. Kit Components

A composition of the ubiquitin hydrolase herein may be formulated in a buffer for stability purposes. The buffer can be composed of inorganic or organic salts and includes, for example, citrate, phosphate, or Tris buffer, depending on the pH desired.

Further, the composition of the ubiquitin hydrolase may be one component of a kit, which also contains an immobilized antibody to a ubiquitin hydrolase as the second component. The antibody may be immobilized as described above regarding modifications to ubiquitin. Such a kit can be used for performing cleavage of fusion protein containing ubiquitin conjugated to the desired protein.

In order to simplify the examples and claims, certain frequently occurring methods will be referenced by shorthand phrases.

"Transfection" refers to the taking up of an expression vector by a host cell whether or not any coding sequences are in fact expressed. Numerous methods of transfection are known to the ordinarily skilled artisan, for example, CaPO4 and electroporation. Successful transfection is generally recognized when any indication of the operation of this vector occurs within the host cell.

"Transformation" means introducing DNA into an organism so that the DNA is replicable, either as an extrachromosomal element or by chromosomal integrant. Depending on the host cell used, transformation is done using standard techniques appropriate to such cells. The calcium treatment employing calcium chloride, as described by Cohen, S. N. *Proc. Natl. Acad. Sci.* (U.S.A.), 69: 2110 (1972) and Mandel et al., *J. Mol. Biol.*, 53:154 (1970), is generally used for prokaryotes or other cells that contain substantial cell-wall barriers. For mammalian cells without such cell walls, the calcium phosphate precipitation method of Graham, F. and ver der Eb, A., *Virology*, 52: 456–457 (1978) is preferred. General aspects of mammalian cell host system transformations have been described by Axel in U.S. Pat. No. 4,399,216 issued Aug. 16, 1983. Transformations into yeast are typically carried out according to the method of Van Solingen, P., et al., *J. Bact.*, 130: 946 (1977) and Hsiao, C. L., et al., *Proc. Natl. Acad. Sci.* (U.S.A.) 76: 3829 (1979). However, other methods for introducing DNA into cells such as by nuclear injection or by protoplast fusion may also be used.

As used herein, the expression "hybridize under stringent conditions" to describe certain DNA sequences encompassed within the scope of this invention refers to hybridizing under conditions of low ionic strength and high temperature for washing, for example, 0.15 M NaCl/0.015 M sodium citrate/0.1% NaDodSO4 at 50° C., or alternatively the presence of denaturing agents such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate, at 42° C. for hybridization. "Hybridize under low stringency" refers to hybridizing under conditions of 20% formamide, 5 X SSPE, 42° C.

"Site-directed mutagenesis" is a technique standard in the art, and is conducted using a synthetic oligonucleotide primer complementary to a single-stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells that harbor the phage. Theoretically, 50 % of the new plaques will contain the phage having, as a single strand, the mutated form; 50% will have the original sequence. The plaques are hybridized with kinased synthetic primer at a temperature that permits hybridization of an exact match, but at which the mismatches with the original strand are sufficient to prevent hybridization. Plaques that hybridize with the probe are then selected and cultured, and the DNA is recovered.

"Operably linked" refers to juxtaposition such that the normal function of the components can be performed. Thus, a coding sequence "operably linked" to control sequences refers to a configuration wherein the coding sequence can be expressed under the control of these sequences and wherein the DNA sequences being linked are contiguous and, in the case of a secretory leader, contiguous and in reading phase. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Linking is accomplished by ligation at convenient restriction sites. If such sites do exist, then synthetic oligonucleotide adaptors or linkers are used in accord with conventional practice.

"Control sequences" refers to DNA sequence necessary for the expression of an operably linked coding sequence in a particular host organism. The control sequences that are suitable for prokaryotes, for example, include a promoter, optionally an operator sequence, a ribosome binding site, and possible, other as yet poorly understood sequences. Eukaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. To effect transformation, the expression system may be included on a vector; however, the relevant DNA may then also be integrated into the host chromosome.

As used herein, "cell," "cell line," and "cell culture" are used interchangeably and all such designations include progeny. Thus, "transformants" or transformed cells" includes the primary subject cell and cultures derived therefrom without regard for the number of transfers. It is also understood that all progeny may not be precisely identical in DNA content, due to deliberate or inadvertent mutations. Mutant progeny that have the same functionality as screened for in the originally transformed cell are included. Where distinct designations are intended, it will be clear from the context.

"Plasmids" are designated by a lower case p preceded and/or followed by capital letters and/or number. The starting plasmids herein are commercially available, are publicly available on an unrestricted basis, or can be constructed from such available plasmids in accord with published procedures. In addition, other equivalent plasmids are known in the art and will be apparent to the ordinary artisan.

"Digestion" of DNA refers to catalytic cleavage of the DNA with an enzyme that acts only at certain locations in the DNA. Such enzymes are called restriction enzymes. and the site for which each is specific is called a restriction site. The various restriction enzymes used here are commercially available and their reaction conditions, cofactors, and other requirements as established by the enzyme suppliers are used. Restriction enzymes commonly are designated by abbreviations composed of a capital letter followed by other letters representing the microorganism from which each restriction enzyme originally was obtained and then a number designating the particular enzyme. In general, about 1 µg of plasmid or DNA fragment is used with about 1-2 units of enzyme in about 20 µl of buffer solution. Appropriate buffers and substrate amounts for particular restriction enzymes are specified by the manufacturer. Incubation of about 1 hour at 37° C. is ordinarily used, but may vary in accordance with the supplier's instructions. After incubation, protein is removed by extraction with phenol and chloroform, and the digested nucleic acid is recovered from the aqueous fraction by precipitation with ethanol. Digestion with a restriction enzyme infrequently is followed with bacterial alkaline phosphatase hydrolysis of the terminal 5' phosphates to prevent the two restriction cleaved ends of a DNA fragment from "circularizing" or forming a closed loop that would impede insertion of another DNA fragment at the restriction site. Unless otherwise stated, digestion of plasmids is not followed by 5' terminal dephosphorylation.

Procedures and reagents for dephosphorylation are conventional (T. Maniatis et al., 1982, *Molecular Cloning: A Laboratory Manual* (New York: Cold Spring Harbor Laboratory, 1982) pp. 133-134).

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is know generally. For example, see R. Lawn et al., *Nucleic Acids Res.* 9:6103-6114 (1981), and D. Goeddel et al., *Nucleic Acids Res.* 8:4057 (1980).

"Southern Analysis" is a method by which the presence of DNA sequences in a digest or DNA-containing composition is confirmed by hybridization to a know, labelled oligonucleotide or DNA fragment. For the purposes herein, unless otherwise provided, Southern analysis shall means separation of digests on 1 percent agarose, denaturation, and transfer to nitrocellulose by the method of E. Southern, *J. Mol. Biol.* 98: 503-517 (1975), and hybridization as described by T. Maniatis et al., *Cell* 15: 687-701 (1978).

"Ligation" refers to the process of forming phosphodiester bonds between two double-stranded nucleic acid fragments (T. Maniatis et al., 1982, supra, p. 146). Unless otherwise provided, ligation may be accomplished using known buffers and conditions with 10 units of T4 DNA ligase ("ligase") per 0.5 µg of approximately equimolar amounts of the DNA fragments to be ligated.

"Preparation" of DNA from transformants means isolating plasmid DNA from microbial culture. Unless otherwise provided, the alkaline/SDS method of Maniatis et al., 1982, supra, p. 90, may be used.

"Oligonucleotides" are short-length, single- or double-stranded polydeoxynucleotides that are chemically synthesized by known methods (such as phosphotriester, phosphite, or phosphoramidite chemistry, using solid phase techniques such as described in EP Pat. Pub. No. 266,032 published May 4, 1988, or via deoxynucleoside H-phosphonate intermediates as described by Froehler et al., *Nucl. Acids Res.*, 14: 5399-5407 [1986]). They are then purified on polyacrylamide gels.

The following examples are intended to illustrate the best mode now known for practicing the invention, but the invention is not to be considered limited thereto.

All literature citations herein are expressly incorporated by reference.

EXAMPLE 1

I. Protein Assay

A. Preparation of 35-S labeled protein substrate for ubiquitin hydrolase

This labeling procedure was carried out in vivo in an *E. coli* strain that contains an integrated bacteriophage T7 RNA polymerase gene and a plasmid containing a gene for a protein substrate to be labeled. The expression of the protein substrate gene was under the control of T7 RNA polymerase promoter, whose sequences were located 5' to the protein substrate gene on the plasmid. The expression of T7 RNA polymerase gene was under the control of the lac promoter of *E. coli*.

DNA fragments encoding yeast ubiquitin fusion polypeptides were synthesized chemically on a DNA synthesizer using the method of Froehler et al., supra. The synthetic ubiquitin fusion gene for human (H2) relaxin B-chain of 32 amino acids (missing the N-terminal amino acid of relaxin B-chain, but adding six amino acids at the junction of ubiquitin and the relaxin chain) is shown in FIG. 1a extending from the sticky ends of XbaI to HindIII. It can be seen from FIG. 1a that the ubiquitin gene has a convenient unique DraIII site at nucleotides 211-216 that can be used to attach DNA encoding various proteins, if the DNA encoding the protein to be attached is linked to the remainder of the nucleotides needed to construct the ubiquitin 3' end and has a DraIII site inserted. This DraIII site was used to synthesize the remaining fusion peptides with N-terminal truncated ubiquitin.

Thus, the truncated synthetic ubiquitin fusion gene for human (H2) relaxin B-chain of 33 amino acids is shown in FIG. 1b extending from the internal DraIII site (sticky end) of ubiquitin to a HindIII site (sticky end) at the end of the relaxin chain. Similarly, the truncated gene for ubiquitin with a gene for a cysteine dipeptide at its 3' end was constructed extending from the ubiquitin sticky end DraIII site to a sticky end HindIII site at the 3' end of the fragment. Also, the truncated gene for ubiquitin fused at its 3' end to the gene for human (H2) relaxin B-chain with 29 amino acids (truncated at its 3' end by four amino acids) was synthesized in the same way, from the internal sticky end DraIII site of ubiquitin to a sticky end HindIII site at the 3' end of the fragment. Finally, the truncated gene for ubiquitin fused at its 3' end to the gene for human (H2) relaxin A-chain with 24 amino acids was synthesized in the same way, from the internal sticky end DraIII site of ubiquitin to a sticky end HindIII site at the 3' end of the fragment. The nucleotide sequence of human relaxin (H2) A-chain can be found in European Pat. Pub. No. 112,149 published Jun. 27, 1984.

Figure 1D:
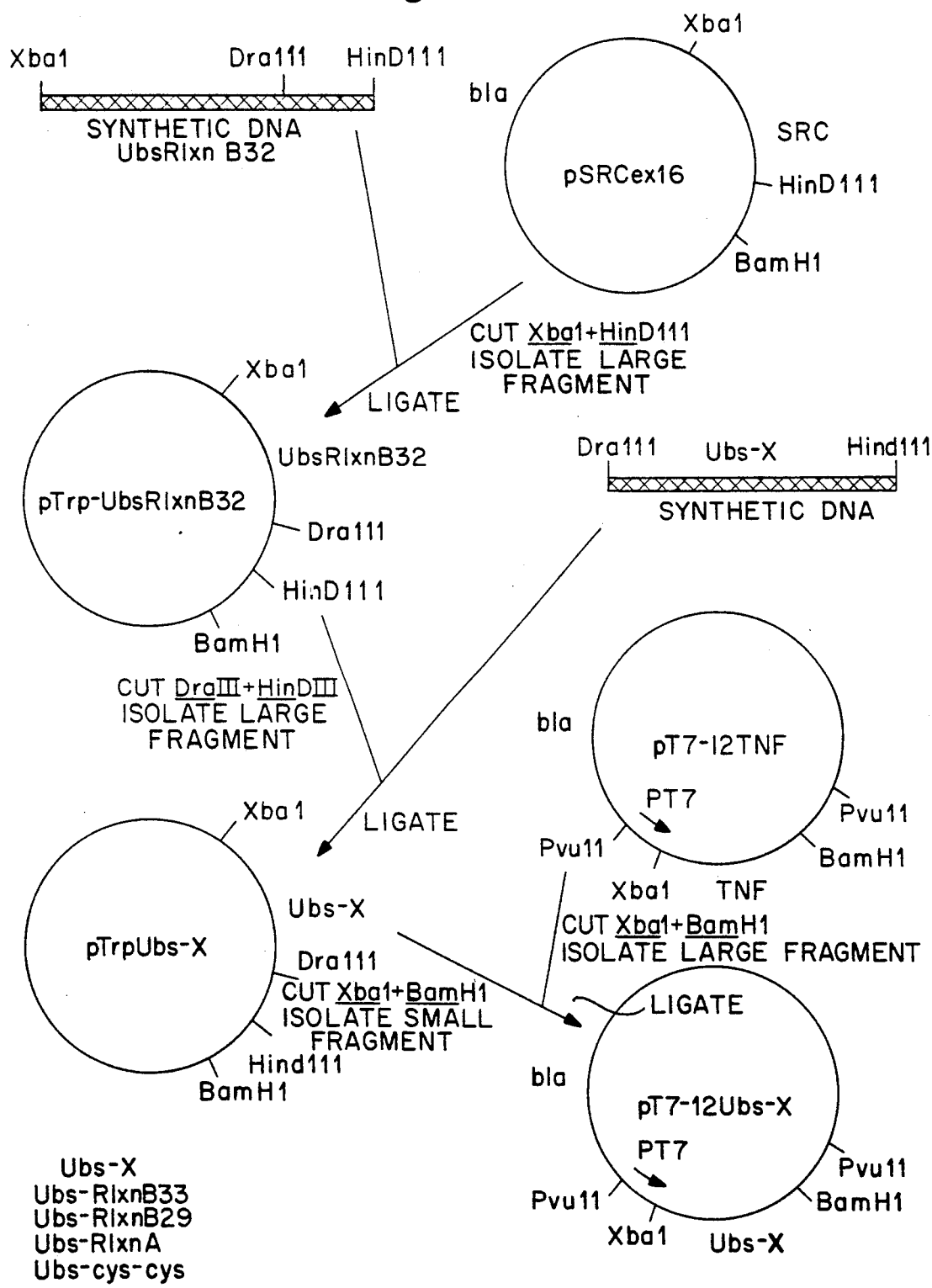
FIG. 1d depicts the construction from pT7-12TNF of several vectors containing ubiquitin fusion polypeptides used in the assay for the ubiquitin hydrolase activity. The pTrpUbs-X series of plasmids are commercially useful for producing ubiquitin fusion polypeptides in large quantities.

FIGS. 1c and 1d show the construction of the vectors encoding the ubiquitin protein substrates with the various synthetic relaxin chains. First, plasmid pT7-2 was obtained from United States Biochemical Corporation. The plasmid DNA was cleaved with PvuI and religated. The DNA was used to transform competent bacteria and clones were screened for inversion of the PvuI fragment. One such inverted clone was called pT7-12. The purpose of this construction was to prevent high-level expression of the beta-lactamase gene, which otherwise would be transcribed under the control of the phi 10 promoter. pT7-12 was cleaved with HincII and BamHI and the large fragment isolated.

A second plasmid, pTrpXAPTNF, was prepared from pBR322 and contains the tumor necrosis factor (TNF)-encoding gene under the control of the trp promoter. The construction of this gene is described fully in EP Pub. No. 168,214, published Jan. 15, 1986, the disclosure of which is incorporated herein by reference. This plasmid was cleaved with HpaI and BamHI and the small fragment was isolated. This small fragment was then ligated to the large fragment from PT7-12, to form the plasmid, pT7-12TNF, which contains the TNF-encoding gene and the XbaI site within the trp leader ribosome binding site. The construction of pT7-12TNF is depicted in FIG. 1c.

The plasmid pSRCex16 (described by J. P. McGrath and A. D. Levinson, Nature, 295: 423-425 [1982]) was cleaved with XbaI and HindIII and the large fragment isolated. The synthetic DNA shown in FIG. 1a (UbsRlxnB32) was ligated with this large fragment to yield the plasmid pTrpUbsRlxnB32, the construction of which is shown in FIG. 1d. This plasmid was cut with XbaI and BamHI and the small fragment was isolated. The plasmid pT7-12TNF was cleaved with XbaI and BamHI and the large fragment was isolated and ligated to the small fragment from PtrpUbsRlxnB32. The resulting plasmid was pT7-12UbsRlxnB32, wherein the synthetic DNA fragment is under the control of the pT7 promoter.

The other plasmids, pT7-12Ubs-X, where X is for the cys-cys dipeptide, relaxin B 29 chain, relaxin B 33 chain, or relaxin A 24 chain, were prepared as shown in FIG. 1d by cleaving the ptrpUbsRlxnB32 vector with DraIII and HindIII, isolating the large fragment and ligating it to one of the four synthetic DraIII-HindIII fragments mentioned above (called Ubs-X) to yield the ptrpUbs-X plasmids, where X is defined above, cleaving these plasmids with XbaI and BamHI, isolating the small fragments, and ligating them to the isolated large fragment of the XbaI and BamHI-cleaved pT7-12 TNF plasmid.

Alternatively, the yeast ubiquitin gene (Ozkaynak et al., The EMBO J., 6: 1429-1439 [1987]) was assembled from eight oligonucleotide fragments ranging from 55 to 62 nucleotides in length, with the sequence and order as follows:

```
ubq-1 5'-CTAGAATTA TGCAAATTTT CGTCAAAACT TTAACAGGCA AGACTATCAC CTTAGA
ubq-2 5'-ATTCAACCTCT AAGGTGATAG TCTTGCCTGT TAAAGTTTTG ACGAAAATTT GCATAATT
ubq-3 5'-GGTTGAATCTTCCG ACACTATCGA TAACGTCAAA TCTAAAATTC AAGATAAAGA AGGTAT
ubq-4 5'-CCGGAGGGATA CCTTCTTTAT CTTGAATTTT AGATTTGACG TTATCGATAG TGTCGGAAG
ubq-5 5'-CCCTCCGGATCAAC AGCGTTTGAT TTTTGCTGGT AAGCAACTAG AAGATGGTCG TACCTT
ubq-6 5'-AGTCAGACAAG GTACGACCAT CTTCTAGTTG CTTACCAGCA AAAATCAAAC GCTGTTGAT
ubq-7 5'-GTCTGACTACAACA TCCAAAAGGA GTCGACTCTT CACTTGGTGT TGCGTCTCCG TGGTGGTG
ubq-8 5'-AATTCACCA CCACGGAGAC GCAACACCAA GTGAAGAGTC GACTCCTTTT GGATGTTGT
```

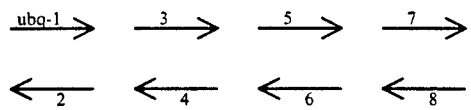

About 30 ng of each oligonucleotide was phosphorylated and ligated together in a single reaction mixture containing 50 mM Tris-HCl (pH 8.0), 10 mM $MgCl_2$, 0.5 mM ATP, 10 units of T4 polynucleotide kinase, and 1000 units of T4 DNA ligase. The resultant DNA duplex was fractionated in a 6% polyacrylamide gel and the DNA band corresponding to the 240 base-pair fragment was excised and electroeluted.

The eluted DNA was extracted with chloroform, precipitated with ethanol, ligated with linkers so as to have XbaI and EcoRI ends, and ligated to the large fragment isolated form a pUC-12 vector (Boehringer Mannheim Biochemicals) cleaved by XbaI and EcoRi.

The sequence of the ubiquitin DNA insert was verified by dideoxynucleotide DNA sequencing analysis.

Similarly, DNA corresponds to the artificial relaxin B-chain gene encoding 38 amino acids was assembled from four synthetic DNA fragments ranging from 57 to 62 nucleotides in length (sequence given below), ligated to EcoRI and HindIII linkers, and then ligated to the large fragment isolated from EcoRI- and HindIII-cleaved pUC-12, and the sequence was verified. These two DNA inserts were excised from their respective plasmids by cleaving with XbaI and EcoRI for the first vector, and with EcoRI and HindIII for the second vector. These two inserts were then ligated together at the common EcoRI sites to yield a XbaI-HindIII fragment. This fragment was ligated with the large fragment isolated from pSRCex16, cleaved by XbaI and HindIII.

sis of T7 RNA polymerase. After another 30 minutes, 20 mg/ml rifampicin was added to give a final concentration of 200 µg/ml to inhibit host RNA polymerase activity. Another 30 minutes later, 25S cysteine (600 Ci/mmole) was added to the culture at the ratio of 0.25 mCi/ml culture to label the proteins or the cys-cys dipeptide.

The labeling was stopped by quenching the culture with cysteine at a final concentration of 50 µg/ml and the bacterial pellet was collected by centrifugation.

The lysis of the cell can be carried out differently depending on the purpose of the cell lysate to be used. The following procedure was used to prepare lysate that contains all soluble $E.$ $coli$ proteins (it contains the labeled protein if it is soluble) in a solution that is compatible with almost all enzymatic processes to be examined under aqueous conditions without further treat- Rlx 1-3 5'-AATTCATCGAAGGTCGTGACTCTTGGATGGAAGAAGTTATCAAACTGTGCGGTCGTGAAC-3'

Rlx 2-4 5'-GAACCAGTTCACGACCGCACAGTTTGATAACTTCTTCCATCCAAGAGTCACGACCTTCGATG-3'

Rlx 5-7 5'-TGGTTCGTGCTCAGATCGCTATCTGCGGTATGTCTACCTGGTCTAAACGTTCTCTGTAG-3'

Rlx 6-8 5'-TAGACATACCGCAGATAGCGATCTGAGCACGATCCTACAGAGAACGTTTAGACCAGG-3'

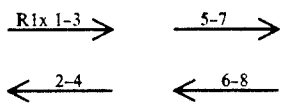

The fusion protein of ubiquitin and relaxin B-chain was prepared by substituting the synthetic DNA sequence existing between the DraIII and HindIII sites of pSRCex16 with the relevant synthetic DNA fragment so that the ubiquitin-encoding gene was 5' to the gene for the polypeptide. The resulting hybrid gene was excised from the pSRCex16-derived plasmid by digestion with XbaI and BamHI, isolated, and inserted into the large fragment isolated from XbaI- and BamHI-cleaved pT7-12TNF.

$E.$ $coli$ K5772 bacteria (deposited in the American Type Culture Collection under accession number 53,635 and containing the T7 RNA polymerase in the $E.$ $coli$ lacZ gene) were made competent and transformed with pT7-12UbsRlxnB32 or one of the pT7-12Ubs-X plasmids, separately. Cells were selected for resistance to carbenicillin.

Each $E.$ $coli$ transformant was grown overnight at 37° C. to saturation in 5 ml of M9 minimal media supplemented with 50 µg/ml each of all amino acids except for cysteine and methionine. (Because of the fast interconversion between cysteine and methionine in vivo, labeling done in the absence of exogenously added methionine will result in the labeling of the methionine residue in the protein. Because of the interconversion, labeling done in the presence of exogenously added methionine will result in the almost nondetectable incorporation of S35 into the methionine residue.) The presence of glucose ensured catabolite repression of the lac promoter controlling T7 RNA polymerase transcription. Fifty µg/ml of carbenicillin was also included to maintain the stability of the plasmid.

The overnight culture was diluted 50-fold into 1 ml of M9 minimal media supplemented with 10 µg/ml of each amino acid except for cysteine and methionine plus 50 µg/ml of carbenicillin.

After three hours of shaking at 37° C., isopropylthio-β-D-galactoside (IPTG) was added to the culture to give a final concentration of 1 mM to induce the synthement. The ratio of various reagents to culture volume was based on a 1-ml labeling culture.

To the collected bacterial pellet, 80 µl of a solution containing 50 mM Tris-Cl (pH 8), 25% (w/v) sucrose was added to resuspend the cells. This step as well as all the following steps were carried out at room temperature.

To the cell suspension, 20 µl of 5 mg/ml of egg white lysozyme freshly dissolved in 0.25 M Tris-Cl (pH 8.0) was added and incubated for five minutes. Forth µl of 0.25 M EDTA (pH 8) was then added to the suspension.

After another five minutes of incubation, cells were lysed by adding 60 µl of the lytic mix containing 50 mM Tris-Cl (pH 8), 50 mM EDTA (pH 8), 0.2% (v/v) NP40. It required between 5 and 10 minutes to obtain complete cell lysis. The lysate was clarified by centrifugation and was ready to be used or could be kept at −°° C. for a long period of time.

B. Ubiquitin Hydrolase Assays

1. Fusion protein cleavage assay

Figure 2:
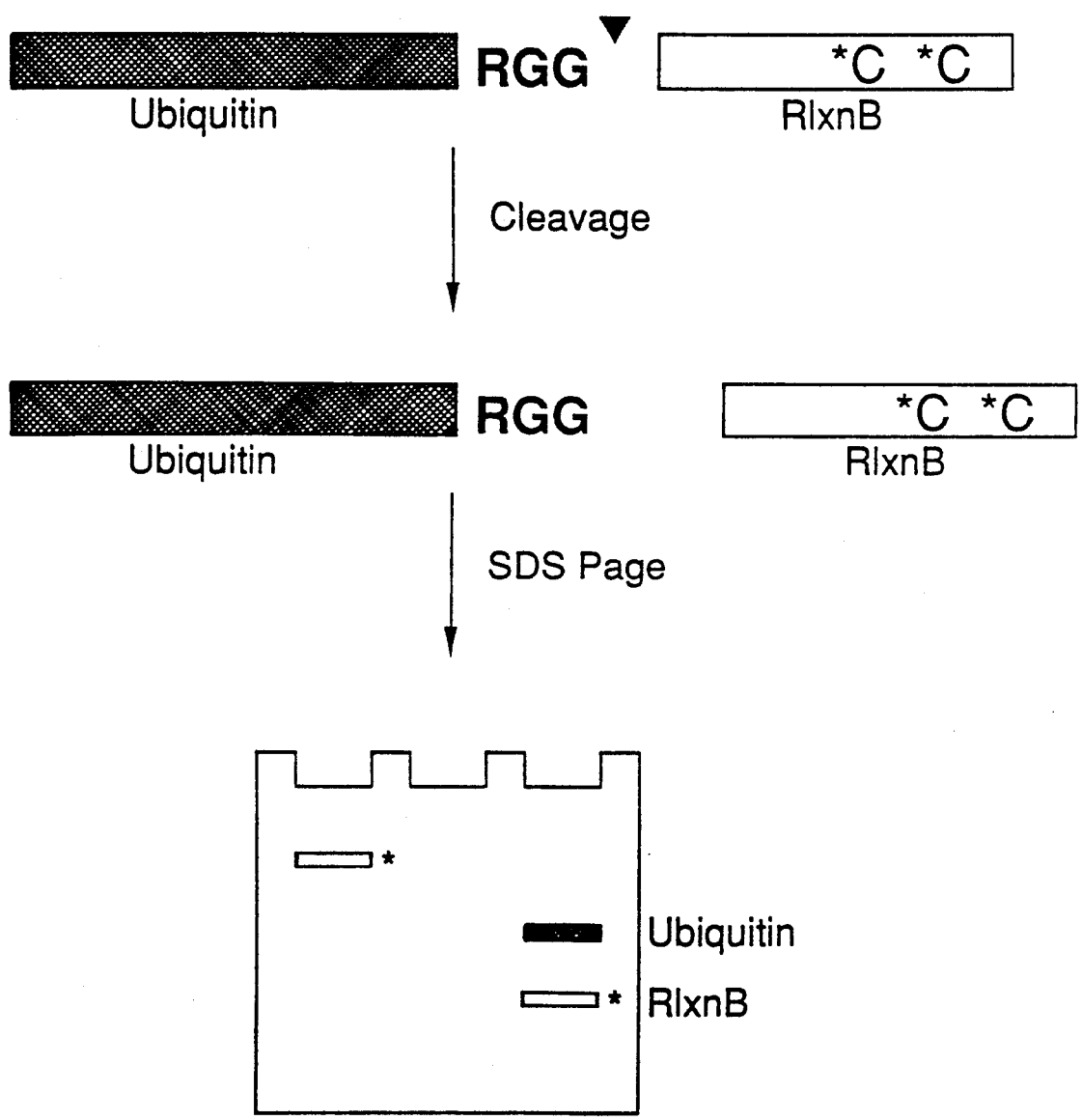
FIG. 2 is a schematic depiction of the ubiquitin hydrolase assay.

All assays were carried out in Eppendorf tubes with a final volume of 25 µl and incubation was at 37° C. for one hour. The reaction mix contained the following:

50 mM Tris-Cl (pH 7.5)
1 mM EDTA (pH 8.0)
10 mM dithiothreitol
1 µl S-35 Cys labeled ubiquitin-relaxin B-chain substrate 2.5 µl ubiquitin hydrolase solution After incubation, the reaction mixtures were mixed with an equal volume of SDS sample buffer, heated to 90° C. for 5 min. The samples were then loaded directly onto a 15% SDS-PAGE gel, and monitored by electrophoresis to resolve the cleaved product from uncleaved substrates. Detection of various labeled protein species was done by drying the gel on a piece of Whatman No. 1 paper and exposing it to X-ray film overnight. A diagram depicting the principle of the assay is shown in FIG. 2, where RGG stands for arg-gly-gly at the carboxy terminus of ubiquitin and C stands for cysteines.

Because the labeled substrate is obtained by in vivo labeling, it is limited in quantity and wit undetermined specific activity. The best way to quantitate the amount of enzyme is to carry out the above reaction with serially diluted enzyme solutions with the same batch of substrate. The fold of dilution where the enzyme activity diminished can be sued as an expression of the relative activity of a particular enzyme solution. The dilution buffer used for this purpose was the reaction cocktail with 50 μg/ml bovine serum albumin without enzyme and substrate.

2. Cleavage by cleaving ubiquitin-Cys-Cys

This assay is identical to the protein cleavage assay in principle except with a different substrate, ubiquitin-cys-cys. The cleaved products, ubiquitin and cys-cys, were separated by acid precipitation instead of SDS-PAGE because cys-cys is soluble in acid while the bigger ubiquitin is not.

All assays were carried out in Eppendorf tubes with a final volume of 25 μl, and incubation was at 37° C. for 20 minutes. The reaction mix contained the following:

50 mM Tris-Cl (pH 7.5)
1 mM EDTA (pH 8.0)
10 mM dithiothreitol
50 μg/ml bovine serum albumin
1 μl S-35 Cys labeled ubiquitin-Cys-Cys substrate
2.5 μl ubiquitin hydrolase solution After incubation, 20 μl of the reaction mixture was spotted onto a GF/C filter disc (2.1 cm) and immediately immersed in 10% (w/v) trichloroacetic acid (TCA) contained in a beaker over ice. Individual filter disc was labeled beforehand with Indian ink for identification after the washing procedures. The beaker was swirled occasionally during a five-minute period. The TCA solution was decanted and filters were further washed with 5% TCA solution. After another five minutes with occasional swirling, the TCA solution was again decanted. Filter discs were rinsed in 95% alcohol to remove TCA and dried under a heat lamp. Individual filter discs were placed into a counting vial, filled with 5 ml of counting fluid, and counted in a scintillation counter. Since the insoluble ubiquitin was retained on the filter disc, hydrolase activity was measured by the decrease of radioactivity retained by the filter disc.

Because the labeled substrate was obtained by in vivo labeling, it is limited in quantity and with undetermined specific activity. The specific activity of the hydrolase is also known at the present time. Therefore, the best way to quantitate the amount of the enzyme is to carry out the above reaction with serially diluted enzyme solutions with the same batch of substrate.

The fold of dilution where the enzyme activity resulted in 60% retention of the original amount of radioactivity can be used as an expression of the relative activity of a particular enzyme solution. The dilution buffer used for this purpose is the reaction cocktail without enzyme substrate and enzyme itself.

Because both protein fusion cleavage assay and cysteine release assay appear to detect the same enzyme, it is easiest to quantitate activity by diluting enzyme solutions to obtain about 50% hydrolysis of the substrate in the cysteine release assay. The relative activity of an enzyme solution was then defined as that fold of dilution necessary to obtain 50% hydrolysis under the standard assay conditions.

II. Purifications and Assay of a Yeast Ubiquitin Hydrolase

All of the purification steps were conducted at room temperature, except for the overnight dialysis and except for storage, which was at 4° C.

A. Fermentation

The yeast strain *Saccharomyces cerevisiae* is grown in a ten-liter fermenter at 30° C. in 2.6% yeast nitrogen base and 1% glucose to an $A_{660}$ of 3-4. Cells are then slowly fed with glucose until the $A_{660}$ reached 50–100.

B. Cell Homogenization

About one kg of the yeast strain fermentation paste was resuspended at 1 g/ml in Buffer A (50 mM Tris-Cl (pH8), 1 mM EDTA, 10% (v/v) glycerol, and 10 mM 2-mercaptoethanol). The resulting suspension was mixed with 0.25 g/ml of glass beads (Sigma G-8893, 106 microns and finer). The cell-glass beads suspension was blended in a Waring blender at top speed for several 2–3 minute-pulses for a total of ten minutes (care must be taken so that the temperature does not rise during this operation). The efficiency of cell breakage can be monitored by measuring protein concentration of the supernatant after a brief centrifugation of the suspension.

After homogenization, the suspension was centrifuged at 12,000 rpm in a Sorvall GSA rotor for about 30 minutes. Pellets were collected and resuspended in Buffer A (at the original 1 g/ml ratio) and were blended again for about five minutes (again, in two-minute pulses). The supernatant was collected after the centrifugation as before and combined with the first supernatant. The combined supernatant was further clarified by centrifugation at 18,000 rpm in a Sorvall SS-34 rotor for 30 minutes. The protein concentration at this stage was about 10 mg/ml or 20 mg/g of original wet yeast paste.

C. Ammonium Sulfate Fractionation

Ubiquitin hydrolase activity was recovered between 33% and 63% saturation of ammonium sulfate. Ammonium sulfate was added directly to the crude, clarified supernatant to give an initial 33% saturation and the pH of the suspension as maintained by adding about 1 μl of 1 M Tris base per g of solid ammonium sulfate added. The supernatant of the 33% saturation was then brought to 63% saturation. About half the protein was removed.

D. DEAE Chromatography

Protein precipitate after 63% ammonium sulfate saturation was collected by centrifuging the suspension from about in a GSA rotor at 12,000 rpm for 30 minutes. Protein precipitate was resuspended in 350 ml of Buffer A and dialyzed against four liters of Buffer A containing 80 mM NaCl for 24 hours (one buffer change in 72 hours). The dialyzed protein solution was loaded onto a DEAE Sephacel column (5×21 cm) equilibrated with Buffer A containing 80 mM NaCl at a flow rate of 400 ml per hour (the flow rate was slowed to about 80 ml per hour). The column was sequentially washed with Buffer A containing 80 mM NaCl, 230 mM NaCl, and 300 mM NaCl. The buffer volume in each wash was about one liter. Almost all the activities eluted in the 300 mM NaCl wash and the column matrix, which was still heavily discolored at this point, was discarded. Active fractions were pooled (about 450 ml) and were subjected to the next column fractionation.

E. Phenyl-Sepharose Chromatography

Solid ammonium sulfate was added to the pooled DEAE fraction at the ratio of ten g per 100 ml of protein solution and loaded directly onto a phenyl-sepharose column (2.5×17 cm) previously equilibrated with Buffer A containing 10% (w/v) ammonium sulfate at a flow rate of about 50 ml per hour. The column was then washed with 100 ml each of Buffer A containing 10% (w/v) and then 5% ammonium sulfate. The enzyme was subsequently eluted with 350 ml of a linearly decreasing gradient composed of Buffer A with 5% ammonium sulfate and Buffer A. Active fractions, which were located in the early 20% of the linear gradient, were pooled (total volume is about 84 ml) and concentrated by ultrafiltration through an Amicon membrane. The concentrate enzyme solution (about 40 ml) was dialyzed overnight against one liter of Buffer B (50 mM Tris-Cl (pH8), 10% (v/v) glycerol, 10 mM 2-mercaptoethanol).

F. Hydroxyapatite Chromatography

The dialyzed enzyme solution was loaded onto a hydroxyapatite column (1.0×7 cm) equilibrated with Buffer B. The column was washed with 10 ml of Buffer B and then eluted with 50 ml of a linear gradient between Buffer B and Buffer B containing 0.5 M ammonium sulfate. It was further washed with 10 ml each of Buffer B containing 0.5 M ammonium sulfate and the 1 M ammonium sulfate. Enzyme activities were located in the gradient and then pooled (total volume is about 8 ml) and dialyzed overnight against Buffer A plus 0.1 M NaCl.

the overall yield at this point was about 20% of the original activity present in the crude lysate and the overall purification was about 15,000 fold.

G. Rechromatography on DEAE Sephacel

A DEAE Sephacel column (0.7×7 cm) was loaded with dialyzed enzyme and the column was equilibrate with Buffer A containing 0.1 M NaCl and then washed with 5 ml of the same buffer. Enzyme activities were eluted with a 30-ml linear gradient between 0.1 M NaCl and 1.0 M NaCl in Buffer A.

The activity was located around 0.3 NaCl as expected and the overall yield at this point was at least 15% of the original activity present in the crude lysate.

H. SDS-PAGE

A reducing SDS-PAGE gel of the recovered activity was prepared and stained with silver stain. Upon visual inspection of the gel and comparison of the relative densities of the bands, it was found that the ubiquitin hydrolase obtained was about 70% pure based on the weight of the total protein in the composition. The major protein species, with molecular weight of about 30,000 daltons, comigrating with hydrolase activities throughout phenyl sepharose, hydroxyapatite and the last DEAE columns, was confirmed by cloning of the gene to be a ubiquitin hydrolase protein.

I. HPLC and Sequencing

The recovered activity from the DEAE column was placed on a 4000 angstrom wide-pore column (100 mm×2 mm in diameter) from Synchrom, Inc. in a Hewlett Packard C4 RP-HPLC 190 M equipped with a 1040 diode array detector. A linear gradient was used of 100% solution A to 60% solution B in 60 minutes, wherein solution A is 0.1% trifluoroacetic acid (TFA) in water and solution B is 0.07% TFA in 1-propanol. The flow rate was 200 µl per minute at room temperature and the peaks were monitored at 214 and 280 nm. All the peaks with 214 nm absorption were collected in the buffer used for the particular assay of the hydrolase activity.

there was one positive assay from the peaks collected that had a 30 kDa molecular weight on a reducing SDS-PAGE gel. One fraction from the DEAE column that was 90% enriched in the 30 kDa protein was digested by adding about 5% Lycine C (Wako) to the fraction in its elution buffer. The digestion was carried out for 24 hours at 37° C. The peptides resulting from the digestion were separated on the C4-HPLC column mentioned above using the same conditions as described above. The separated peptides were sequenced on an Applied Biosystems 470A gas phase sequencer using Edman degradation. The following amino acid sequences were obtained:

1. SDPTATDLIEQELVRVRVA
2. ENVQTFSTGQSEAPEATADTNLHYI
3. NEWAYFDIY
4. NRFDDVTTQ.

III. Cloning and Expression of the Hydrolase Gene

A synthetic DNA probe was synthesized on a DNA synthesizer using the method of Froehler et al., supra. This probe (Probe 1, 53 mer) had the following sequence:

5'-GACCCAACTGCTACTGACTTGATC-
GAACAAGAATTGGTTAGAGT-
TAGAGTTGC-3'

Total genomic DNA was isolated from a yeast strain S1799D (αtrp5 his4 ade6 gal2) of *Saccharomyces cerevisiae* (Yeast Genetic Stock Center, Berkely, Calif.) by the method of Smith et al., *Method enzymol.*, 12: 538–541 (1967). 370 µg of yeast DNA was partially digested with 2.5 units of Sau3AI (New England Biolabs) in 2 ml of reaction mixture. Aliquots were removed at 10, 20, and 30 min., chilled, and inactivated with 20 mM EDTA. The pooled, phenol-extracted DNA was fractionated by centrifugation in 10–50% sucrose gradients in 1 M NaCl, 20 mM Tris-HCl (pH 8.0), and 10 mM EDTA. The sau3AI 10–15-kb fragments (determined by agarose gel electrophoresis) were isolated and ligated into bacteriophage λ Charon 30 cut with BamHI-isolated arms (Maniatis et al., supra).

The resultant ligated DNA was then used to infect an *E. coli* DP50 strain (commercially available) on plates. Ten-thousand plaques were lifted onto non-sterilized nitrocellulose filters (Schleicher and Schuell, BA85, 132 nm diameter). The filters were denatured by contact with a solution of 0.5 M NaOH, 1 M NaCl. Then they were renatured in a solution of Tris, pH 7.5, 3 M NaCl and washed in 2×SSC. After renaturation, the filters were baked for one hour at 80° C. in a vacuum oven. The filters were then treated at 42° C. for five minutes in a prehybridization buffer consisting of 5×SSPE (20×SSPE is prepared by dissolving 174 g of NaCl, 27.6 g of $NaH_2PO_4.H_2$), and 7.4 g of EDTA in 800 ml of water with pH adjusted to 7.4 and volume adjusted to 1 liter; alternatively, SSPE is 0.18 M NaCl, 10 mM $NaPO_4$, 1 Mm NaEDTA, pH 7), 5×Denhardt's solution (1×Denhardt's solution =0.1% Ficoll, 0.1% polyvinylpyrrolidone, 0.1% BSA), 0.1 mM ATP, 0.2 µg/ml sonicated salmon sperm DNA, 20% formamide, and 0.1 % SDS. Then Probe 1, labeled at its 5' end with radioactive phosphorus as described below was added to the prehybridization mixture at a concentration of 2×10$^6$ cpm per ml.

Probe 1 was 5'-end labeled with 32P in a solution containing 0.05 M Tris-HCl pH 7.6, 0.01 M $MgCl_2$, 0.005 M dithiothreitol, 0.1 mM spermidine, 0.1 mM EDTA, 35 µg/ml synthetic Probe 1, 4 mCi/ml gamma 32P ATP (about 5000 Ci/mmol), and 10 U polynucleotide kinase for 30 min. at 37° C. The labeled DNA was phenol/CHCl₃ extracted, ethanol precipitated, and resuspended in water. Incorporated 32P was determined by spotting an aliquot of the probe solution on a DEAE filter disc and washing extensively with 0.5N ammonium formate, followed by liquid scintillation counting.

The filters were incubated with probe 1 for one hour at 42° C. Then the filters were removed from the probe solution and washed three times in 2×SSC plus 0.1% SDS at 37° C. for 15 min. The filters were exposed to x-ray film for three hours at −70° C. Positive plaques were chosen and grown in liquid media for DNA.

After growth of the phage DNA, the phage were cleaved with several restriction enzymes. The resulting fragments were placed on nitrocellulose filters and treated with prehybridization buffer and Probe I as described above. The probe was found to hybridize to a 1.2 kb SalI to BamHI fragment on phage λ 7. This fragment was isolated from λ 7 by cleaving the SalI and BamHI.

M13mp18 and M13mp19 bacteriophages, available from New England Biolabs, were cleaved with SalI and BamHI and the large fragment was isolated. The fragment from λ 7 was ligated with the large fragments from M13mp18 and M13mp19 such that the fragment from λ 7 was under the control of the lac promoter. The resulting constructs were plated on JM101 on X-Gal plates (Messing and Viera, *Gene*, 19: 269–276 [1982]). Colorless plaques were picked and single-stranded DNA templates containing the fragment in the M13mp18 bacteriophage were sequenced by the dideoxy-chain termination method of Sanger et al., supra, from the SalI site to the BamHI site and vice-versa, using a synthetic phage-specific primer.

After the determination of about 500 bp in each direction, new primers were designed based on the determined sequence and the sequence was extended on additional 500-bp. A 2-kb SalI-EcoRI fragment, shown by restriction mapping to be adjacent to the SalI-BamHI fragment, was cloned into M13mp18 and the DNA sequence was determined for about 500 bp. Samples were separated by electrophoresis on 5% polyacrylamide/8M urea "thin" gels. Gels were dried onto Whatman 3MM paper and exposed to Kodak x-ray film for varying lengths of time.

FIG. 3 shows the nucleotide sequence determined for the fragment from the SalI end to within about 300 bases of the BamHI end, as well as the imputed amino acid sequence of the 26-kd yeast ubiquitin hydrolase YUH-1 and the positions of various restriction sites and the position of probe 1. FIG. 4 shows the direction of the sequencing.

FIG. 5 shows not only the predicted amino acid sequence of YUH-1, but also its flanking region from HindIII to BamHI, based on the partial sequence of the 2-kb EcoRI-SalI fragment flanking the SalI-BamHI fragment containing lambda and yeast DNA. The location of the three sequenced peptides is indicated with stars. The 53-mer probe sequence is shown below the correct DNA sequence. Mismatches are indicated as lower case letters. The probe is 87% identical with the correct DNA sequence.

The M13mp19 bacteriophage containing the SalI-BamHI hydrolase-encoding insert was used to transform *E. coli* strain SR101 (commercially available), which was grown using as the culture media LB Broth.

The production of protein was induced by adding 1 mM of IPTG to the culture medium.

Lysis of the SR101 cells was performed using the lysate procedure described in the protein assay section herein for preparing the labeled protein substrate for ubiquitin hydrolase from K5772.

The cell lysate was clarified by centrifugation and then assayed for activity by the fusion polypeptide assay described above. The assay showed detectable ubiquitin hydrolase activity by both assays, indicating that the DNA sequences cloned encoded hydrolase protein and were induced by IPTG.

EXAMPLE II

DNA fragments encoding yeast ubiquitin were synthesized chemically on a DNA synthesizer using methoxyphosphoramidites. The yeast ubiquitin gene was synthesized connected to the gene coding for human (H2) relaxin B chain of 32 amino acids, to yield the sequence shown in FIG. 1a, to human (H2) relaxin A chain of 24 amino acids, to prorelaxin, and to the human (H2) relaxin B chain of 33 amino acids to yield the sequence shown in FIG. 1b. Each fragment was designed so as to have a sticky-end XbaI and BamHI site at the ends. The prorelaxin construct is described in European Pat. Pub. 260,149 published Mar. 16, 1988. The DNA sequence for A-chain relaxin is provided in EP Pub. No. 112,149, supra. The disclosure of both of these patent publications are incorporated by reference herein.

The synthetic genes were separately cloned into the large fragment after XbaI and BamHI digestion of the plasmid trp 207-1*tetxap, described in detail in European Pat. Pub. 260,149. The ubiquitin-fusion polypeptide gene was ligated such that the ubiquitin fusion polypeptide gene was under the control of the trp promoter of the trp 207-1*tetxap plasmid. *E. coli* strain MM294 (commercially available) was transformed with the resulting plasmids and the synthesis of the fusion proteins was induced by adding indoleacrylic acid to the culture medium. SDS-PAGE analysis using silver straining under reducing conditions revealed a prominent protein band. Upon Western blotting analysis this band reacted with an antibody directed against the appropriate relaxin moiety. The band was found to correspond to the correct molecular weight in each instance.

The culture of each transformant is then fermented, harvested, and run through an affinity chromatography column on which are immobilized anti-ubiquitin monoclonal antibodies. The material bound to the column is eluted and run through a column having the ubiquitin hydrolase purified as described above adsorbed thereto. The eluent from the column is passed through the affinity chromatography column on which are immobilized the anti-ubiquitin monoclonal antibodies. The first fractions containing separately the various relaxin polypeptides are obtained and pooled, free from the cleaved ubiquitin, the ubiquitin fusion polypeptide, and all cellular debris.

EXAMPLE III

Figure 6:
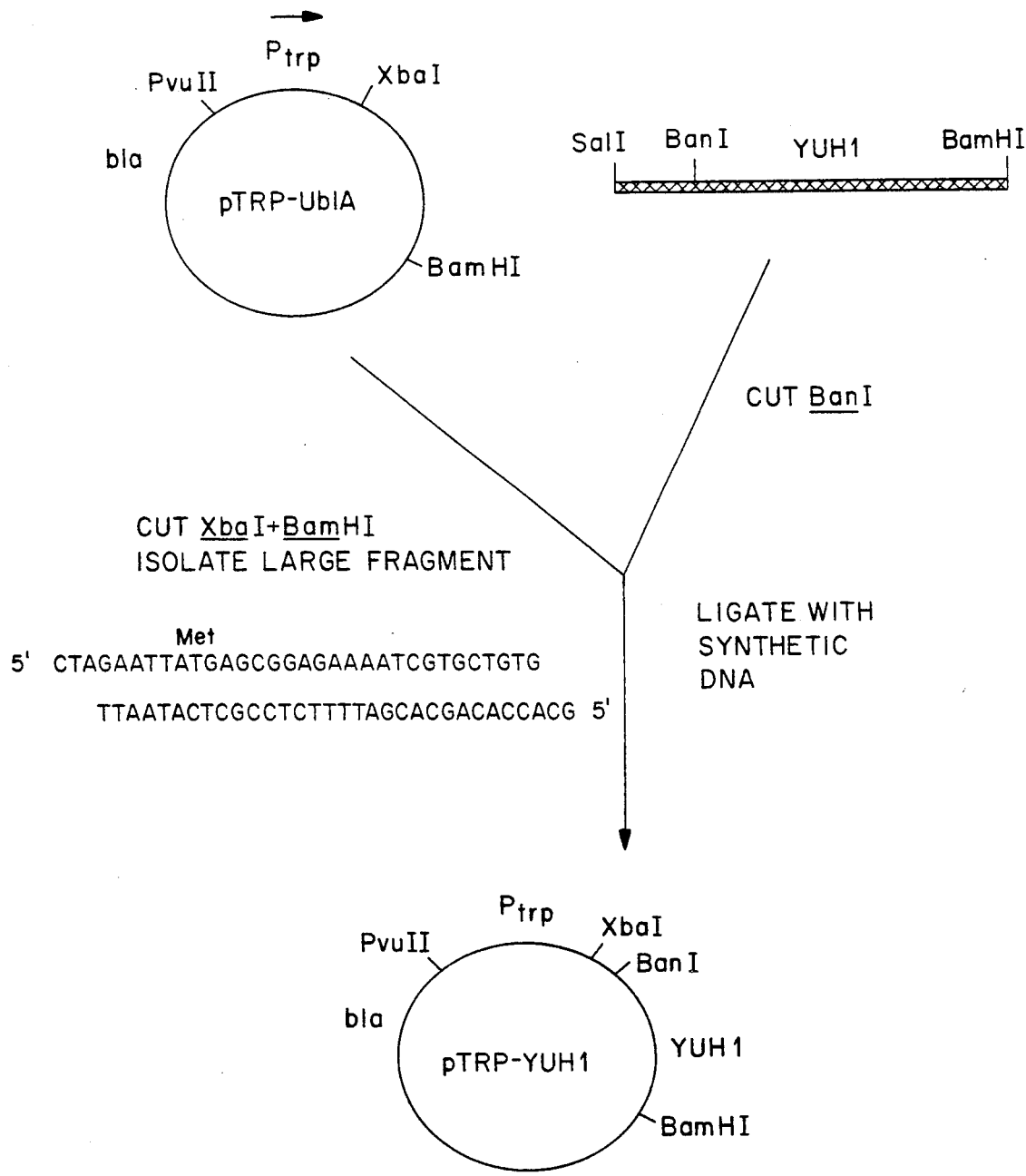
FIG. 6 depicts the construction of the expression plasmid pTRP-YUH from pTRP-UbiA used to transform E. coli to overproduce ubiquitin hydrolase.
Figure 7:
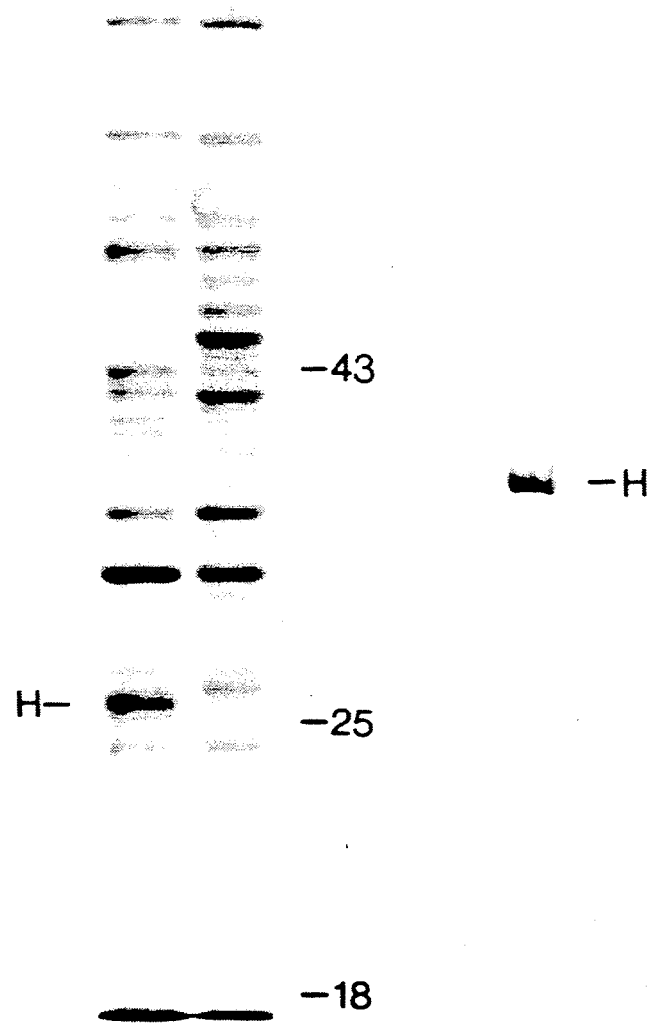
FIG. 7 depicts SDS-polyacrylamide gels of the protein products produced when E. coli is transformed with pTRP-YUH and grown under inducing conditions (lane a) or non-inducing conditions (lane b), and purified to homogeneity (lane c). "H" designates the location of the band for ubiquitin hydrolase (at 26 kD).

The plasmid of Example II where the ubiquitin-relaxin A-chain synthetic DNA was inserted into the large fragment of XbaI- and BamHI-digested trp 207-1*tetxap is designated pTRP-UbiA. pTRP-UbiA was digested with XbaI and BamHI and the large fragment was isolated. The 1.2 kb SalI-BamHI fragment from the Charon 30 clone (Example I) was isolated and cleaved at the unique BanI site. Synthetic DNA encoding an *E. coli* ribosome binding site sequence and a XbaI site at its 5' end (its sequence shown in FIG. 6) was ligated to the BanI site so that the 5' untranslated end of the cloned ubiquitin hydrolase gene was replaced by the binding site. The resulting XbaI-BamHI fragment was cloned into the large fragment of pTRP-UbiA such that the gene was placed under the control of the trp promoter of the plasmid. The construction of this plasmid, designated pTRP-YUH, is shown in FIG. 6.

pTRP-YUH was transformed into *E. coli* strain MM294 and grown in either LB media or M9 minimal casamino acids media (lacking tryptophan) to saturation at 37° C. Samples were lysed at 90° C. in SDS sample buffer as described herein and electrophoresed through a 10% SDS polyacrylamide gel, followed by staining in Coomassie brilliant blue. FIG. 7 shows the results. Lane (a) is growth of the *E. coli* strain in M9 minimal casamino acids media (lacking tryptophan) and lane (b) is growth in LB media.

The *E. coli* transformed with pTRP-YUH in M9 medium overproduced the 26-kd ubiquitin hydrolase, as determined from the prominent band on the SDS-PAGE gel shown in FIG. 7. The same plasmid in LB media did not produce a 26-kd ubiquitin hydrolase band.

The ubiquitin hydrolase was isolated and purified as follows: About 60 g of *E. coli* cells was resuspended in 120 ml of Buffer A. The cell suspension was sonicated in a sonicator for 3.5 minutes and clarified by centrifugation. The clarified supernatant was loaded directly onto a DEAE Sephacel column (2.5×16 cm) equilibrated with Buffer A containing 0.1 M NaCl. The column was washed with Buffer A containing 0.1 M NaCl, then developed with a linear gradient of 0.1 M NaCl to 0.5 M NaCl. The activity was located by the cysteine release assay and pooled (60 ml). Enough ammonium sulfate was added to the pooled enzyme solution to give a 10% (w/v) final concentration.

The enzyme solution was then loaded onto a phenyl-Sepharose column (2.5×12 cm) equilibrated with Buffer A and 10% (w/v) ammonium sulfate. After a wash with Buffer A and 10% (w/v) ammonium sulfate, the column was developed with a decreasing gradient of 10% to 0% (w/v) ammonium sulfate in Buffer A. the hydrolase activity co-eluted with the major protein peak and was essentially pure after this step, as determined from SDS-PAGE analysis, shown as lane 3 in FIG. 7. All active fractions were pooled and dialyzed versus Buffer A and 50% glycerol for storage.

The purified protein was capable of cleaving ubiquitin protein fusions and was active in the cysteine release assay, using the assays described in Example I.

EXAMPLE IV

This example illustrates the ability of the ubiquitin hydrolase to cleave proteins in vivo in *E. coli*.

Figure 8:
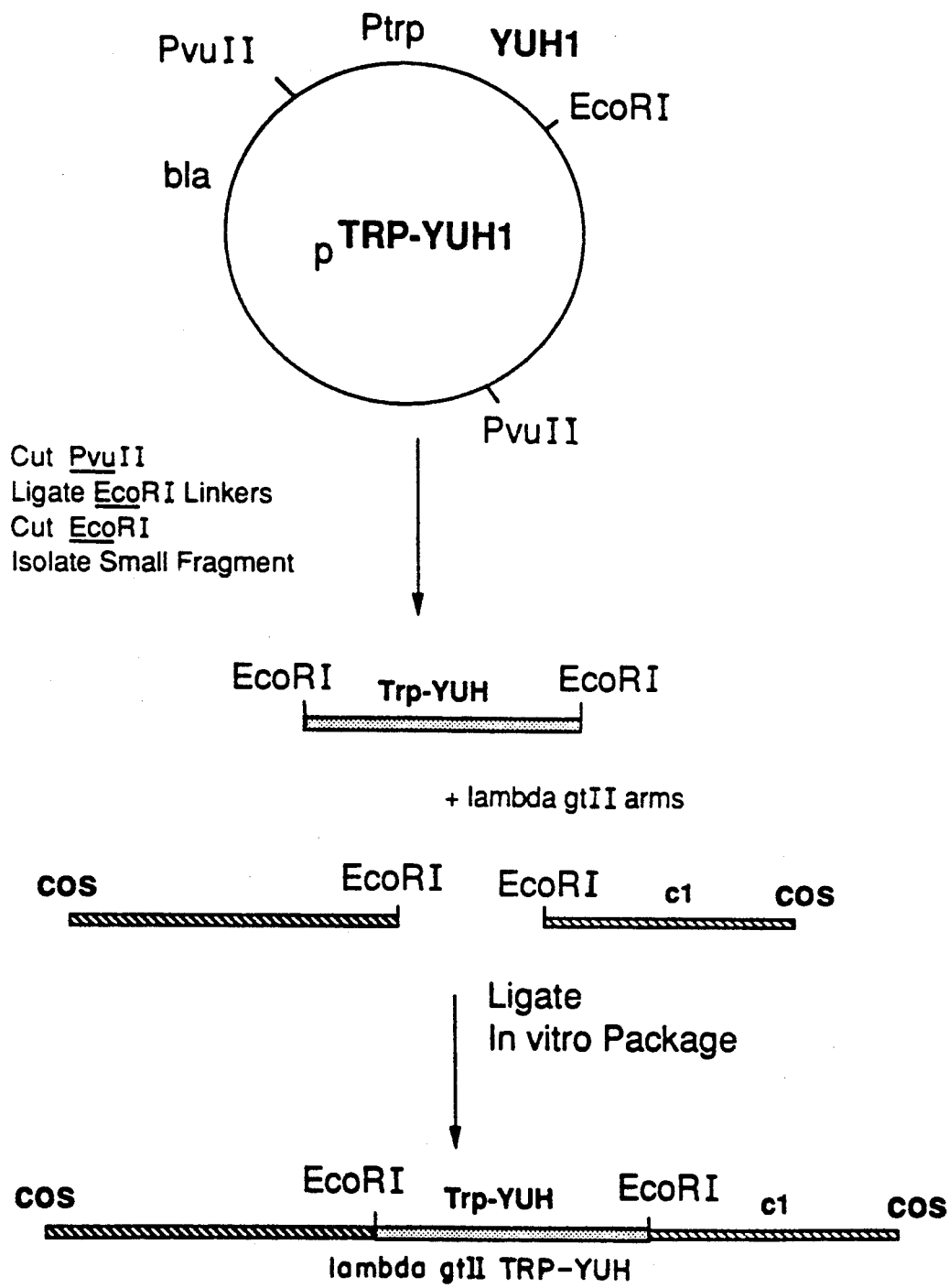
FIG. 8 depicts the construction of lambda gt11 TRP-YUH that is made form PTRP-YUH and is integrated into the genome of an E. coli strain.

A DNA fragment containing the trp promoter and YUH-1 gene from plasmid pTRP-YUH shown in FIG. 6 was cloned into lambda gt11 phage. The construction of lambda gt11 TRP-YUH is shown in FIG. 8. The recombinant phage was used to lysogenize T7 RNA polymerase-containing strain K5772. the resulting strain, designated *E. coli* strain K5808, which contains a gene coding for ubiquitin hydrolase in its genome, was deposited in the American Type Culture Collection under ATCC No. 53,832 on Nov. 30, 1988.

A plasmid pT7-12 containing a ubiquitin-relaxin A fusion protein was prepared as depicted in FIGS. 9-13, starting with pT7-12 and ptrpST2HGH.

Figure 9:
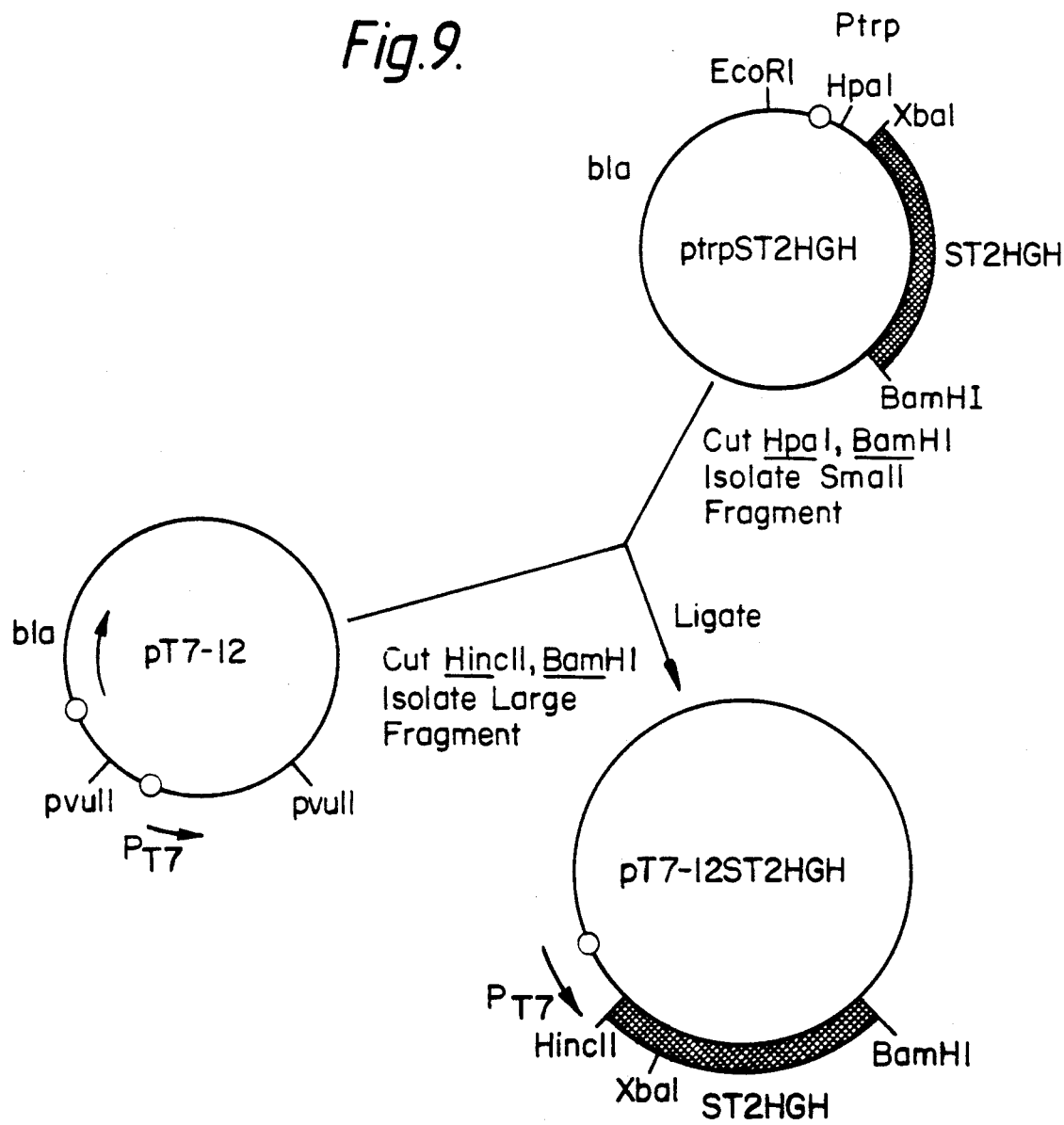
FIG. 9 depicts the construction of pT7-12ST2HGH, an intermediate plasmid that supplies the STII signal and the phi 10 promoter recognized by T7 polymerase.

Construction of pT7-12ST2HGH (FIG. 9)

Plasmid pT7-12 (described in Example I) was digested with HincII and BamHI and the large vector fragment isolated. Plasmid ptrpST2HGH (EP 177,343) was digested with HpaI and BamHI and the small hGH coding fragment isolated. The two fragments were ligated to produce pT7-12ST2HGH.

Construction of pT7-12ST2TPA-1 (FIG. 10)

Plasmid pT7-12ST2HGH was digested with XbaI and BamHI and the large vector fragment isolated. Plasmid pΔRIPA° (EP 93,619, containing the *E. coli* trp promoter/operator and the human t-PA gene) was digested with BstXI and BamHI and the small fragment (the t-PA gene) isolated. The same plasmid was also cleaved with BstXI and PstI and the 383-bp fragment isolated. These three fragments were ligated with two double-stranded synthetic DNA fragments A (encoding the N-terminus of the STII signal) and B (encoding the C-terminus of the STII signal fused to the N-terminal seryl residue of t-PA) to yield pT7-12ST2TPA-1.

Fragment A

Fragment B

Figure 11:
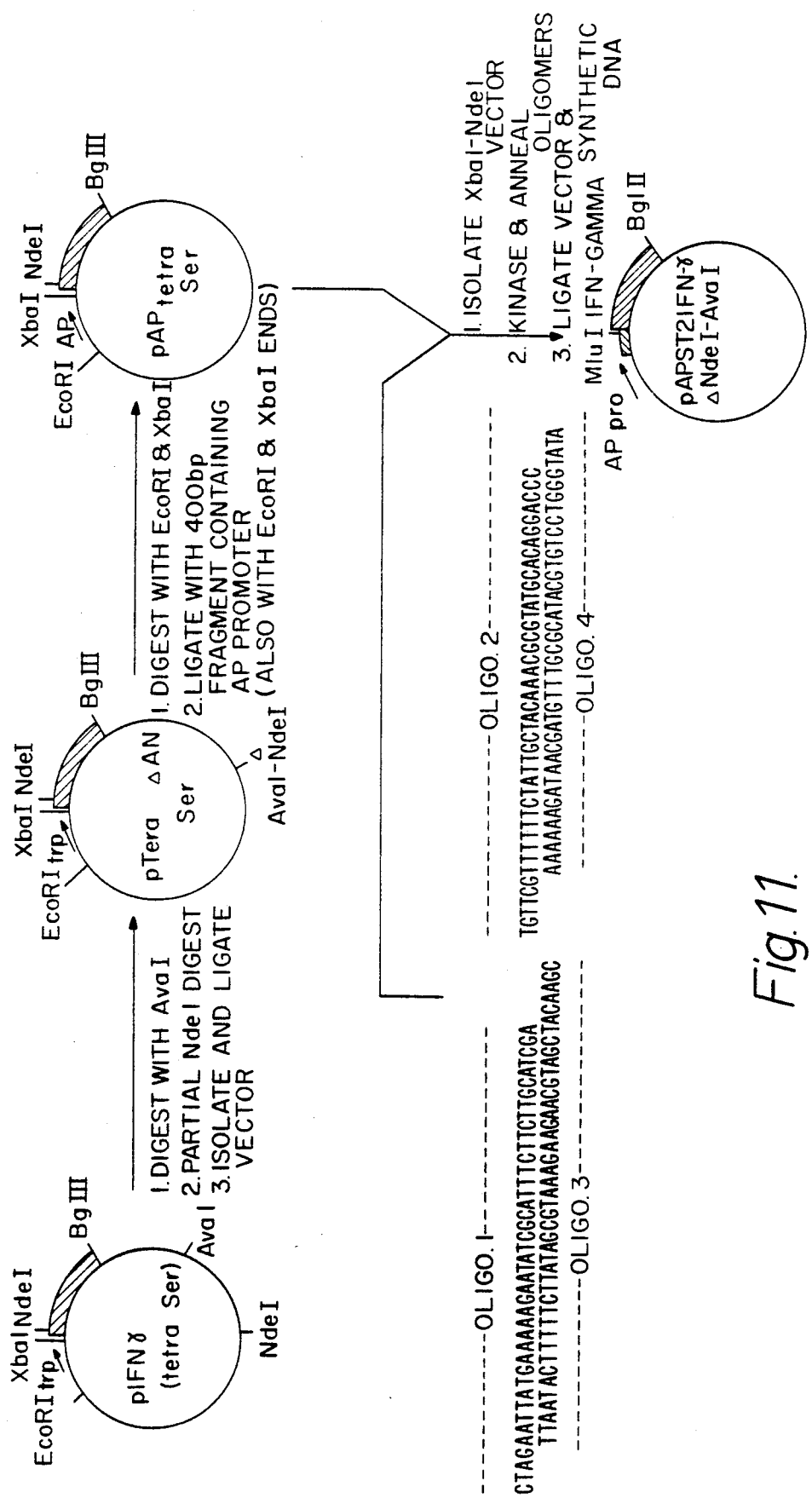
FIG. 11 discloses the construction of pAPST2IFN-γΔNdeI-AvaI.

Construction of pAPST2IFN-γΔNdeI-AvaI (FIG. 11)

Plasmid pIFN-γ (tetra-Ser) (de la Maza et al., *Infection and Immunity* 55: 2727 [1987]) was digested with AvaI and then partially digested with NdeI. The vector was treated with the Klenow fragment of DNA polymerase I to repair the sticky ends and then isolated and ligated to itself to provide pTetraSer ΔAN. Plasmid pAPH-1 (P. Gray et al., *Gene* 39:247 [1985]) was digested with EcoRi and XbaI, and the 400 basepair EcoRI-XbaI fragment was isolated and ligated into EcoRI- and XbaI-digested pTetraSer ΔAN to provide plasmid pAP tetraSer. Plasmid pAP tetraSer was digested with XbaI and NdeI and the vector was isolated. Synthetic oligonucleotide fragments of sequence shown in FIG. 11 were kinased, annealed and ligated into the XbaI-NdeI vector obtained from plasmid pAP tetraSer to provide plasmid pAPST2IFN-γΔNdeI-AvaI, which contains a promoter from the alkaline phosphatase gene (Y. Kikuchi et al., *Nucleic Acids Res.* 9:5671 [1981]) and the *E. coli* secretory signal of heat signal enterotoxin II (R. N. Picken et al., *Infection and Immunity* 42:269 [1983]).

Figure 12:
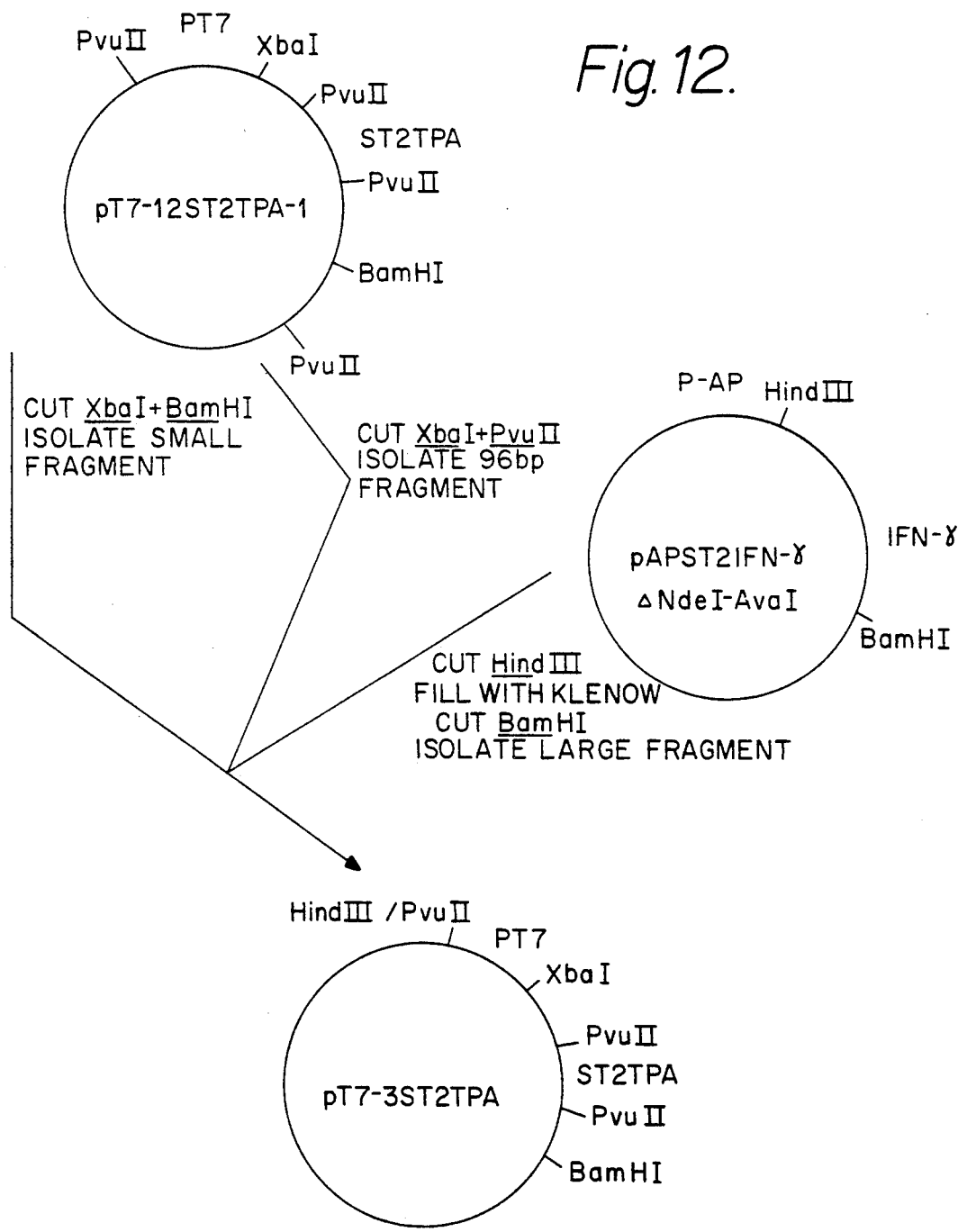
FIG. 12 depicts the construction, from Pt7-12ST2TPA-1 and pAPST2IFN-γΔNdeI-AvaI, of pT7-3ST2TPA.

Construction of pT7-3ST2TPA (FIG. 12)

pT7-12ST2TPA-1 is digested with SbaI and BamHI and small fragment isolated. The same plasmid is digested with XbaI and PvuII and a 96-bp fragment isolated.

pAPST2IFN-γΔNdeI-AvaI is cleaved with HindIII, treated with Klenow DNA polymerase I to fill in the sticky end, and cleaved with BamHI, and the large fragment is isolated.

The XbaI-BamHI small fragment, the 96-bp fragment, and the large fragment from pAPST2IFN-γΔNdeI-AvaI are ligated together to give the plasmid pT7-3ST2TPA.

Figure 13:
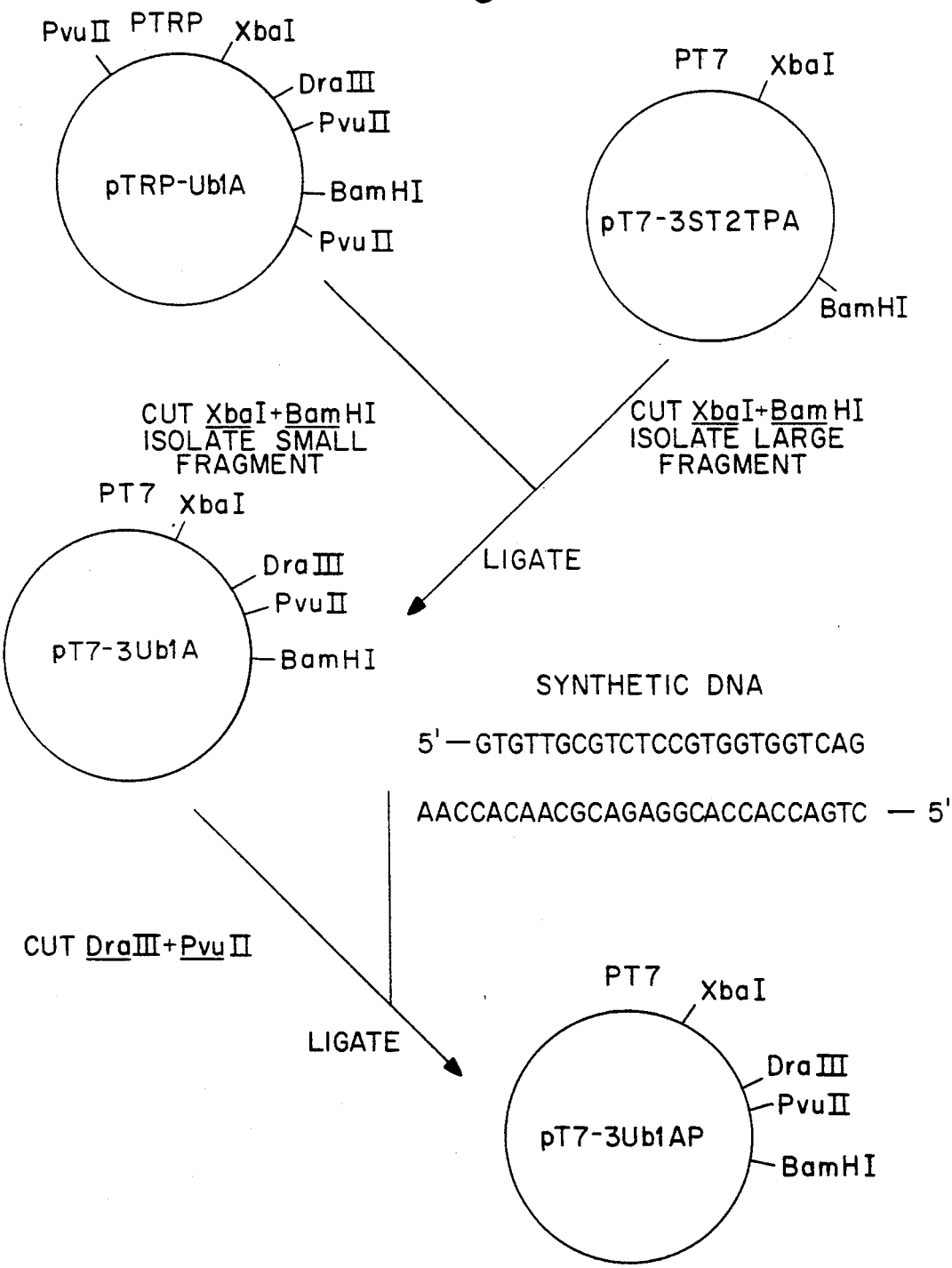
FIG. 13 depicts the construction, from pT7-3ST2TPA and pTRP-UbiA, of pT7-3UbiAP, which contains the ubiquitin-relaxin A fusion synthetic DNA fragment driven by the phi 10 promoter.

Construction of pT7-3UbiAP (FIG. 13)

pT7-3ST2TPA is digested with XbaI and BamHI and the large fragment isolated. pTRP-UbiA was digested with XbaI and BamHI and the small fragment was isolated. This small fragment was ligated to the large fragment from pT7-3ST2TPA. The resulting plasmid, pT7-3UbiA, was digested with DraIII and PvuII and ligated to the synthetic DNA fragment indicated in FIG. 13 to yield pT7-3UbiAP.

Construction of pT7-12UbiB pT7-12ST2TPA-1 is digested with XbaI and BamHI and the large fragment is isolated and ligated to a synthetic DNA fragment encoding the ubiquitin-relaxin B-29 fusion protein and having XbaI and BamHI sticky ends, to produce pT7-12UbiB.

Transformation and Cleavage

Strain K5808 was transformed with either of pT7-3UbiAP or pT7-3UbiB. In addition, strain K5772 was transformed with a plasmid encoding relaxin A-chain alone (under the control of pT7 promoter) as a control, and the cell supernatant was analyzed by SDS-PAGE gel. Also the supernatant of the relaxin A-chain fusion treated with ubiquitin hydrolase purified from *E. coli* from Example III was also analyzed.

The K5772 and K5808 strains were grown in M9 minimal salts media containing 50 μg/ml of each common amino acid except methionine, cysteine, and tryptophan, and in 50 μg/ml of ampicillin to maintain the appropriate plasmid. Incubations were at 37° C. for K5772 derivatives and 32° C. for K5808 derivatives. Cultures were grown to an OD of 0.4, at which time IPTG was added to a concentration of 1 mM and incubation was continued for 30 min. Rifampicin was added to 200 μg/ml and the culture was incubated an additional 30 min. 35S-cysteine was added (10 μCi/ml, 600 Ci/mmol), and the culture was pulse-labeled for the indicated time. Samples were either immediately lysed in SDS sample buffer (10% glycerol, 5% beta-mercaptoethanol, 2.3% SDS, 0.0625 Tris-HCl pH 6.8, 0.04% Bromphenol Blue) at 90° C. for 5 min., then placed on ice, or the labeled cells were rapidly pelleted in eppendorf tubes and frozen in ethanol/dry ice. When pulse-chase experiments were performed, chloramphenicol (100 μg/ml) was added immediately after the pulse and incubation was continued, with pulse-chase samples taken at 10, 20 and 30 minutes. Thus, the polypeptides, labeled in vivo by the T7 RNA polymerase, were followed by pulse chase and analyzed on a reducing SDS-PAGE gel.

Figure 14:
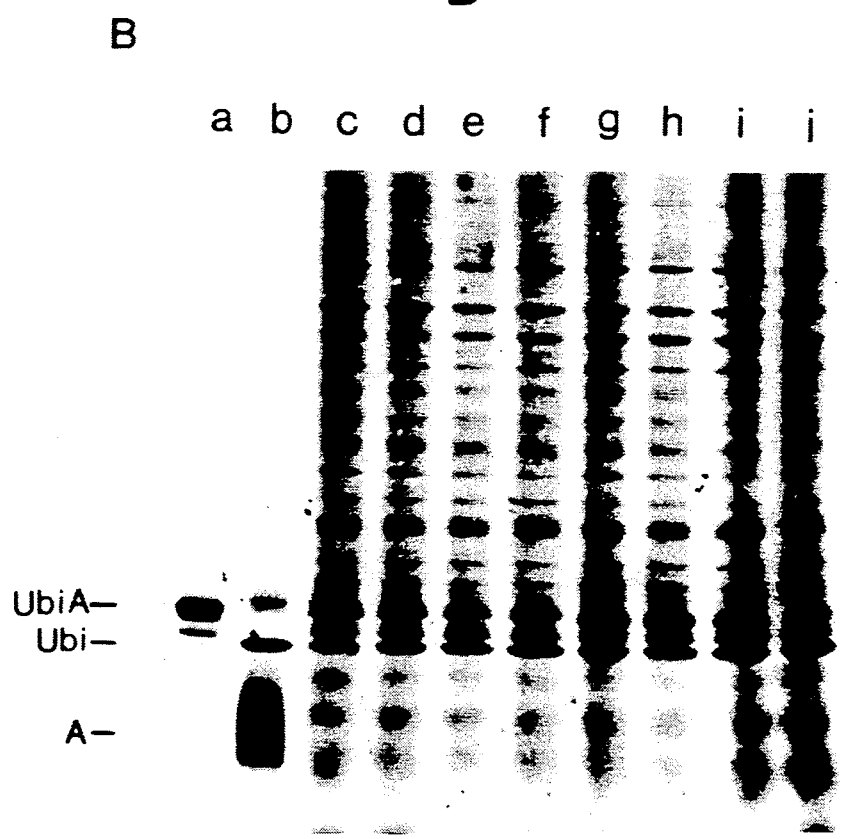
FIG. 14 depicts SDS-polyacrylamide gels of the protein products produced upon in vivo cleavage of ubiquitin-relaxin A and ubiquitin-relaxin B fusion polypeptides expressed from pT7-3UbiAP and pT7-12UbiB in an E. coli strain that has integrated into its genome lambda gt11 TRP-YUH, expressing the YUH-1 gene.

The SDS-PAGE results are shown in FIG. 14, where Lane (a) is the cell supernatant of labeled relaxin A fusion in *E. coli* strain K5772, Lane (b) is the supernatant of labeled relaxin A fusion treated in vitro with purified ubiquitin hydrolase from *E. coli*, Lanes (c)–(f) are relaxin A fusion label in strain K5808 containing the ubiquitin hydrolase gene, with (d)–(f) chased for 10, 20, and 30 min., respectively, and Lanes (g)–(j) are relaxin B fusion labeled in strain K5808, with (h)–(j) chased for 10, 20, and 30 min., respectively. The positions of ubiquitin monomer and the relaxin A polypeptide are indicated.

The strain K5772 lacking the YUH-1 gene as well as the integrated lambda phage produced only the fusion proteins. However, the K5808 strain containing the YUH-1 gene produced fusion proteins that are chased into ubiquitin-sized polypeptide. The carboxyl-terminal extension polypeptide relaxin A-chain was apparently degraded, as was the relaxin B-chain.

EXAMPLE V

This example shows the effect of changing the amino acid at position 76 of ubiquitin or at the N-terminus of the polypeptide fused to the ubiquitin (position 77).

The ubiquitin gene has a convenient unique SalI site 5' to the unique DraIII site that was used to link DNA encoding fusion proteins. The DNA fragments given below were linked to the remainder of the nucleotides needed to reconstitute the ubiquitin 3' end and have a SacII site inserted. To this end, pT7-12UbiAP containing DNA encoding ubiquitin fused to relaxin A was cleaved with SalI and BamHI and ligated with one of the following synthetic DNA fragments having a SalI sticky end at the 5' end and a BamHI sticky end at the 3' end on the top strand. (Nucleotides contributed by the vector that encode the remainder of the polypeptide are underlined.) pT7-12UbiAP is prepared by cleaving pT7-12ST2TPA-1 with XbaI and BamHI, isolating the large fragment, cleaving pT7-3UbiAP with XbaI and BamHI and isolating the small fragment, and ligating these two fragments together.

```
(Gly 77) 5'-TCGACT CTT CACTTGGTGT TGCGTCTC CG CGGTGGTGGA TCC CCG GGCG-
         3'-    GAGAA GTGAACCACA ACGCAGAGGC GCCACCACCT AGGGGCCCGC-
            Ser Thr Leu His Leu Val L eu Arg Leu Ar g Gly Gly Gly Ser Pro Gly G-

AGCTC GAATT CACTGGCCGT CGTTTT ACAA CGTCGTGA-3'
            TC GAGCTT AA GTGACCGGCA GCAAAATGTT GCAGCACT-5'
            lu Leu Glu Ph e Thr Gly Arg Arg Phe Thr T hr Ser OP (Val 76) 5'-TCGACT CTT CACTTGGTGT TGCGTCTC CG CGGTGTCGGA TCC CCG GGCG-
         3'-    GAGAA GTGAACCACA ACGCAGAGGC GCCACAGCCT AGGGGCCCGC-
            Ser Thr Leu His Leu Val L eu Arg Leu Ar g Gly Val Gly Ser Pro Gly G-
```

-continued

```
          AGCTC GAATT CACTGGCCGT CGTTTT ACAA CGTCGTGA-3'
          TCGAGCTT AA GTGACCGGCA GCAAAATGTT GCAGCACT-5'
           lu  Leu Glu Ph e Thr Gly Arg Arg Phe Thr T hr Ser OP (Cys 76) 5'-TCG ACT CTT CAC TTG GTG T TGC GTC TCC CG CGG TTG CTA G        -3'
         3'-    GAG AA GTG AAC CAC A ACG CAG AGG C GCC AAC GAT C CTA G-5'
             Ser Thr Leu His Leu Val L eu Arg Leu Ar g Gly Cys (Pro 77) 5'-TCG ACT CTT CAC TTG GTG T TGC GTC TCC CG CGG TGG TCC G GGA TCC CCGG-
         3'-    GAG AA GTG AAC CAC A ACG CAG AGG C GCC ACC AGG C CCT AGG GGCC-
             Ser Thr Leu His Leu Val L eu Arg Leu Ar g Gly Gly Pro  Gly Ser Pro G-

GCGAGCTCGA ATTC ACTGGC CGTCGTTTTA CAACGTCGTG A-3'
          CGCTC GACCT TAAGTGACCG GCAGCAAAAT GTTGCAGCAC T-5'
           ly Glu Leu Gl u Phe Thr Gly Arg Arg Phe T hr Thr Ser OP
```

Another set of constructions is prepared by cleaving pT7-3UbiAP with DraIII and BamHI, isolating the large fragment, and ligating it to a synthetic DNA fragment encoding one of the following polypeptides:

(Asp 77) ubiquitin-Asp-amino acids 2-29 of relaxin B-chain (Gln 77) ubiquitin-Gln-amino acids 2-24 of relaxin A-chain.

Also (Glu 77) [ubiquitin-Glu-pentapeptide-amino acids 2-33 of relaxin B-chain] was prepared as described above (FIG. 1b and Example I).

In addition, plasmids were constructed such that the synthetic DNA for the fusion polypeptide, driven by the pT7 promoter, encoded a methionine or cysteine residue at position 77 (at the N-terminus of the fused polypeptide).

Strain K5772 was transformed with each of the above plasmids, the protein substrates were labeled, and the fusion protein in vitro cleavage assay was performed as described in Example I.

Efficient cleavage was achieved for the Glu 77, Asp 77, Gln 77, Cys 77, Gly 77, and Met 77 constructions. If proline was inserted at this position 77, however, no cleavage was observed, consistent with the in vivo results of Bachmair et al., Science, 234: 179-186 (1986). In addition, substitution of valine or cysteine at position 76 of ubiquitin (the C terminus) blocked cleavage, showing the importance of the glycine residue at position 76.

EXAMPLE VI

Finley et al., Cell, 48: 1035-1046 (1987) found that deletion of the yeast penta-ubiquitin gene rendered the cell sensitive to environmental stress. Removal of the YUH-1 gene should therefore produce the same or a more severe phenotype, because the cell should have no way to generate ubiquitin monomer, and therefore be ubiquitin minus.

Figure 15:
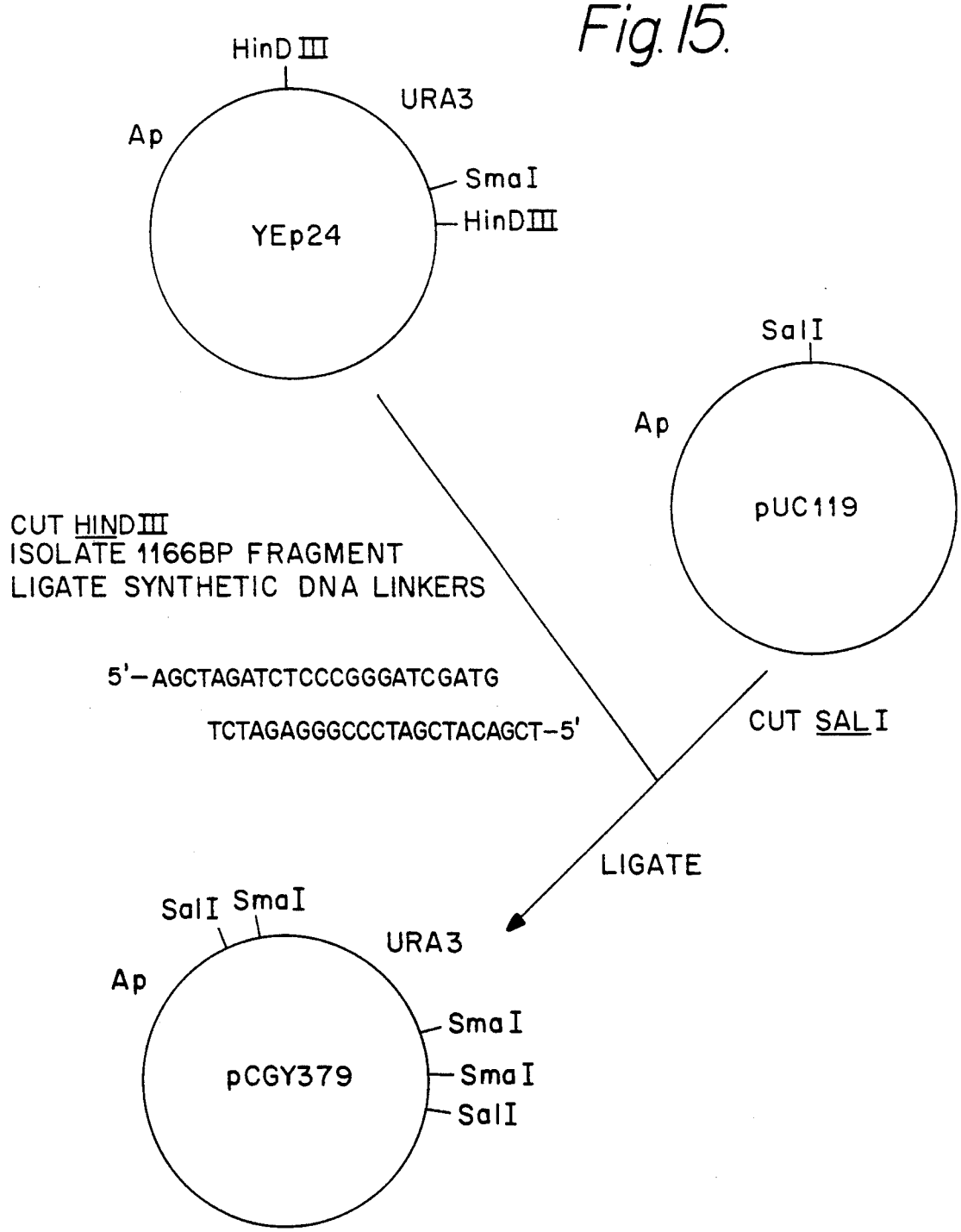
FIG. 15 depicts the construction of pCGY379.
Figure 16:
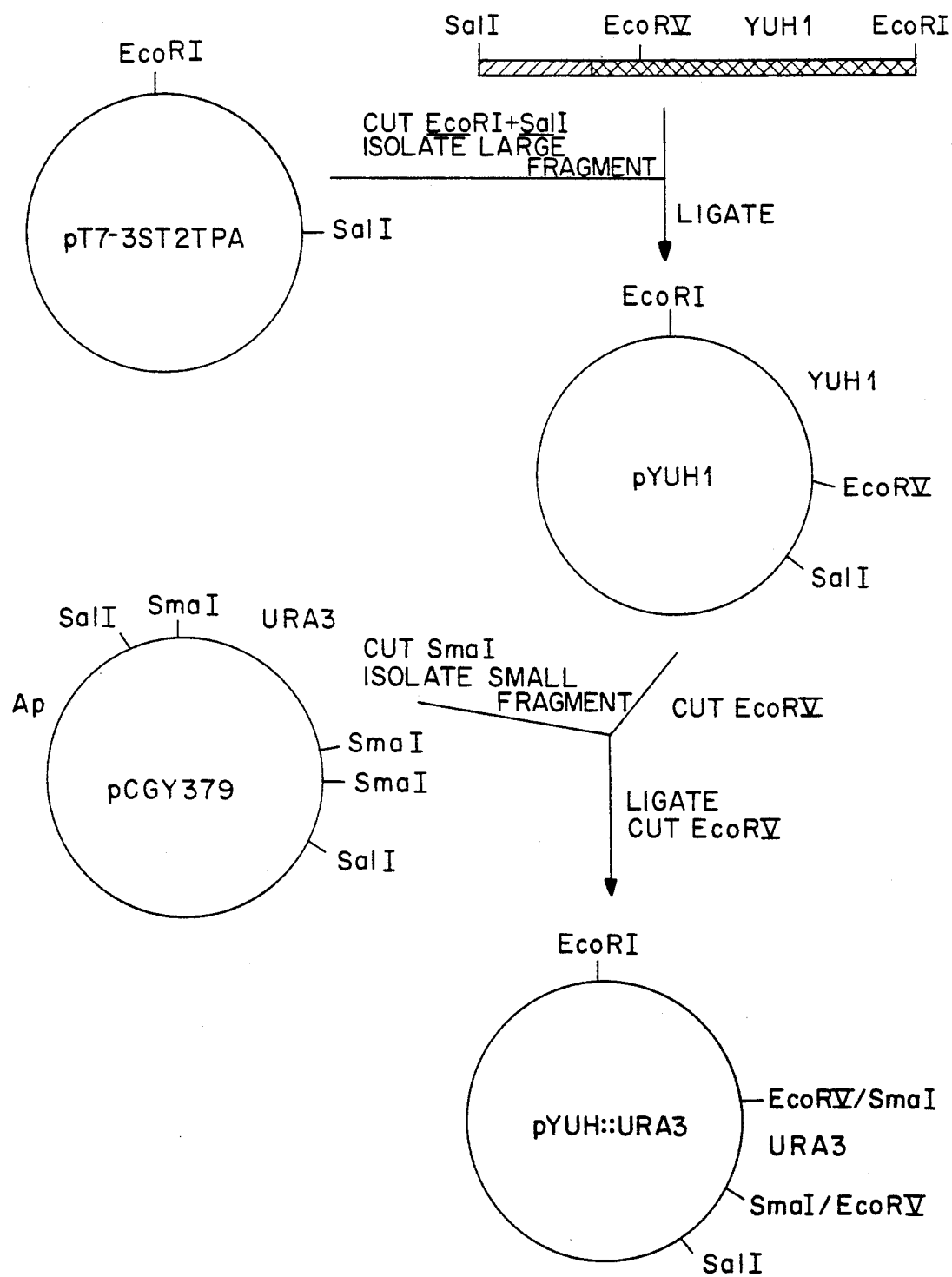
FIG. 16 depicts the construction, from pT7-3ST2TPA and pCGY379, of pYUH::URA3 that contains the interrupted YUH-1 gene.

Therefore, the YUH-1 gene was interrupted with the Ura3 gene as described below. The final plasmid, pYUH::URA3, was prepared from pCGY379, the construction of which is described below, and pT7-3ST2TPA described above.

pCGY379 was prepared by cleaving YEp24 (New England Biolabs) with HindIII and isolating the 1166-bp fragment. The fragment was ligated with the synthetic linkers described in FIG. 15. pUC119 (commercially available) was cleaved with SalI and ligated with the 1166-bp fragment having the linkers. The resulting plasmid was pCGY379, and its construction is illustrated in FIG. 15.

pYUH::URA3 was prepared as follows: pTRP-YUH (described above) was cleaved with SalI and EcoRI and the small fragment containing the YUH1 gene was isolated. pT7-3ST2TPA was cleaved with EcoRi and SalI and the large vector fragment was isolated. These two fragments were ligated to obtain Plasmid pYUH1. pYUH1 was cleaved with EcoRV. pGCY379 was cleaved with SmaI and the small fragment (1.1 kb) containing the yeast URA3 gene was isolated. This SmaI fragment and the cleaved pYUH1 plasmid were ligated, and the ligated product was cleaved with EcoRV, to yield pYUH::URA3 containing the URA 3 gene within the YUH-1 gene. The construction is shown in FIG. 16.

Figure 17:
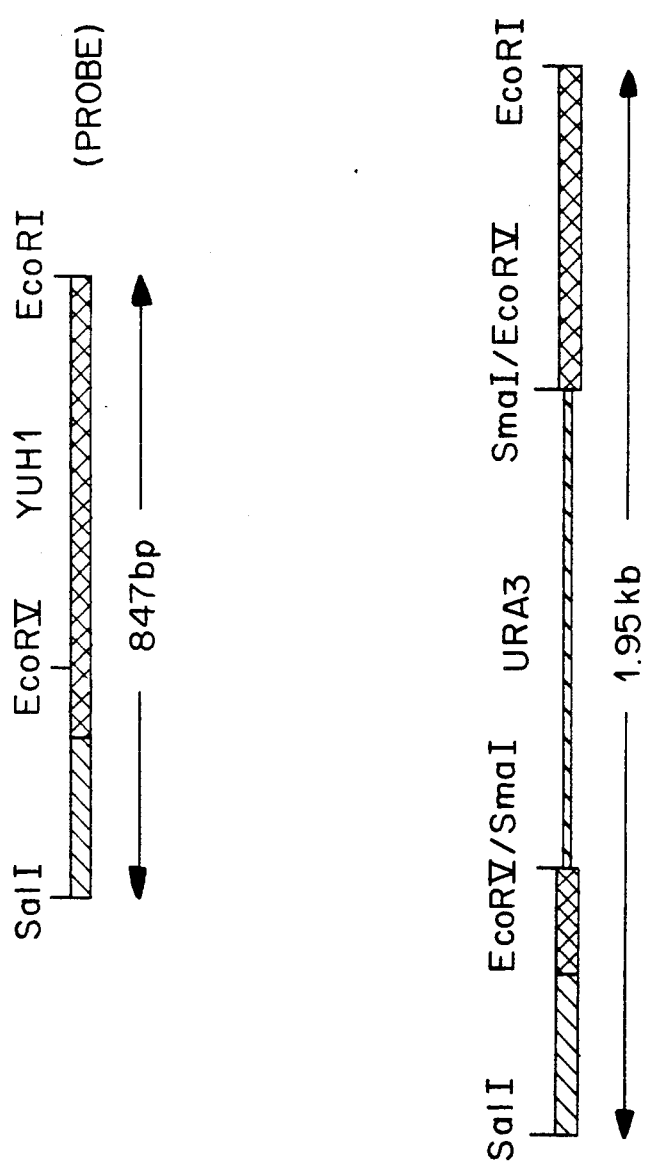
FIG. 17 depicts the SalI to EcoRI 0.847 and 1.95 kb fragments for the uninterrupted and interrupted YUH-1 genes, respectively.

The pYUH::URA3 plasmid was cleaved with SalI and EcoRI. The small fragment, a 1.95-kb fragment, is shown in FIG. 17, along with the SalI-EcoRI 847-bp fragment containing the uninterrupted YUH-1 gene used as a hybridization probe.

A diploid ura3/ura3 yeast auxotroph (a/α ura3-52) may be prepared by mating the haploids DBY747 (MAT a ura3-52) and DBY746 (MAT α ura3-52) by a standard mating technique. These haploids are available from the Yeast Genetic Stock Center in Berkley, Calif. The resulting diploid may be transformed with the 1.95-kb fragment as described by Rothstein, Meth. Enzymol., 101: 202-211 (1983). URA+ diploids are selected and sporulated. Rothstein, supra. The spores are dissected and tested for growth and URA phenotype. All spores, whether URA+ or URA-, are viable and grow into haploid yeast colonies. DNA is prepared from the parental diploid strain, the URA+ diploid, a URA+ haploid spore from the URA+ diploid, and a urahaploid spore from the URA+ diploid, cleaved with SalI and EcoRI, and Southern blotted using the 847-bp SalI-EcoRI fragment from the YUH-1 gene as a probe, labeled as described below, to screen for the insertion of the URA3 gene into the YUH-1 gene.

The 847-bp SalI-EcoRI DNA fragment is labeled by random primed DNA synthesis. A mixture containing 8 μg/ml DNA in 10 mM Tris-HCl pH 7.4, 10 mM MgCl$_2$, 100 μM dATP, dGTP, and TTP, 4 mCi/ml alpha 32P dCTP, and 40 μl/ml calf thymus primer is heated to 100° C. for 2 min., then cooled on ice. Klenow enzyme (400 U/ml) is added and incubation is for one hour at room temperature. The mixture is phenol/CHCl$_3$ extracted and ethanol precipitated. Incorporated radioactivity is determined as described in Example I. The labeled probe is heated to 100° C. for 5 minutes and chilled on ice prior to addition to hybridization reactions. The hybridization of the probe is carried out as described in Example I.

The resulting Southern blots are shown in FIG. 18, where Lane (a) is the parental strain (ura- diploid), (b)

is the URA+ diploid, (c) is a URA+ haploid, and (d) is a ura− haploid.

The 847-bp parental SalI-EcoRI fragment is seen in the parental diploid, URA+ diploid, and ura− haploid. The 2-kb insertion fragment is only present in the URA+ haploid and the URA+ diploid. These experiments confirm the presence of URA3-interrupted YUH-1 gene in the haploid spores as well as in one chromosome of the diploid parental transformant.

Extracts of the YUH-1-negative URA+ diploid and haploid clones are assayed for ubiquitin-protein in vitro cleavage activity as described in Example I. The results show that the YUH-1-negative clones contain nearly wild-type levels of enzyme. Since the URA3 gene interrupts the YUH-1 gene at the 35th amino acid and no AUG translation start codon is found in the YUH-1 gene until the very C-terminus, no active protein could be made from the split YUH-1 gene. Therefore, there exists at least a second gene, YUH-2, which codes for a second yeast ubiquitin hydrolase. This gene is not related to YUH-1 at the DNA sequence level because no second band of hybridization is seen on the FIG. 18 Southern blot of DNA from the YUH-1-negative URA+ haploid when the YUH-1 gene is used as a probe at low stringency. The gene YUH-2, therefore, encodes a second yeast ubiquitin hydrolase.

This second yeast ubiquitin hydrolase protein is cloned and expressed by first fermenting the URA+ haploid whose Southern Blot is shown in Lane (c) and purifying and partially sequencing the hydrolase contained therein (for purposes of designing a probe) using the method described in Example I, Sec. II. Once at least a partial sequence is obtained, it may be used to prepare a synthetic probe, which is used to screen a yeast library as described in Example I, Sec. III. The DNA fragment hybridizing to the probe is isolated from the relevant phage, clone into M13mp19 and/or M13mp18 bacteriophage, and sequence as described in Example I. The hydrolase-encoding fragment is then linked to a suitable promoter such as trp, and to a ribosome binding site, transformed into an *E. coli* strain and induced for expression as described, for example, in Example III for YUH-1.

SUMMARY

In summary, a gene (YUH-1) has been cloned form the yeast, *Saccharomyces cerevisiae,* that codes for a catalytic activity that processes ubiquitin-protein fusions. The gene codes for a 26-kd protein and, as for most yeast genes, contains no introns. The YUH-1 gene can be overexpressed in E. coli in active form and purified to homogenity and the enzyme is capable of cleaving ubiquitin fusions intracellurlarly in *E. coli.*

When isolated from yeast, ubiquitin hydrolase purifies as a complex containing at least two other proteins.

Gene interruptions of the YUH-1 gene are not lethal to haploid yeast. Indeed, the levels of ubiquitin hydrolase as assayed by cysteine release assay are near normal in such strains. The yeast cell appears to contain a second ubiquitin hydrolase gene YUH-2.

The yeast ubiquitin hhydrolase is specific for cleaving the peptide bond following gly76 of ubiquitin fusion proteins. Alternation of a single amino acid in the ubiquitin moiety at position 76 appears to inhibit cleavage. However, the enzyme is relatively insensitive to the size of the C-terminal extension or to the residue following the cleavage site, except for proline.

In vivo synthesis of ubiquitin fusion proteins that are purified and process in vitro will allow the synthesis of proteins with specified amino termini. This process may be of particular utility for making small peptides that, due to their size, may be rapidly degraded intracellularly. Because ubiquitin hydrolase is also active in cleaving ubiquitin from ubiquitin-protein conjugates, purified hydrolase is extremely useful for deubiquitinating eukaryotic proteins in vitro prior to performing activity assays and/or sequence determination, because the presence of ubiquitin may interfere with these processes.

What is claimed is:

1. An isolated nucleic acid sequence encoding a yeast ubiquitin hydrolase of the YUH-1 family and having the nucleotide sequence shown in FIG. 5.

2. An isolate DNA sequence comprising a sequence that hybridizes, under stringent conditions of 50% (vol.-/vol.) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate, at 42° C., to the DNA sequence of FIG. 5 and encoding the biological activity of yeast ubiquitin hydrolase.

3. A nucleic acid sequence encoding a biologically active yeast ubiquitin hydrolase with an amino acid sequence having at least about 80% sequence identity with that of the ubiquitin hydrolase amino acid sequence shown in FIG. 5.

4. The nucleic acid sequence of claim 3 wherein the amino acid sequence of the ubiquitin hydrolase has at least about 90% sequence identity with that of the ubiquitin hydrolase amino acid sequence shown in FIG. 5.

5. The nucleic acid sequence of claim 3 wherein the hydrolase has the ability to hydrolyze a ubiquitin-polypeptide conjugate at the amide bond linking the ubiquitin and polypeptide.

6. The nucleic acid sequence of claim 3 wherein the molecular weight of the ubiquitin hydrolase is from about 26,000 to about 29,000 on a reducing SDS-PAGE gel.

7. The nucleic acid sequence of claim 3 further comprising a promoter operably linked to said nucleic acid sequence.

8. The nucleic acid sequence of claim 3 further comprising an origin of replication operative in a unicellular organism.

9. An expression vector comprising the nucleic acid sequence of claim 3 operably linked to a control sequence recognized by a host transformed by the vector.

10. The vector of claim 9 wherein the control sequence is a promoter 5' to the nucleic acid sequence.

11. A bacterial, yeast, or mammalian host cell transformed with the expression vector of claim 9.

12. The host cell of claim 11 wherein the cell is bacterial and the vector comprises a signal sequence for secretion of the hydrolase.

13. The host cell of claim 12 that is *E. coli.*

14. The host cell of claim 11 that is mammalian or yeast.

15. The sequence of claim 1 that is a cDNA sequence.

16. The sequence of claim 3 further comprising a signal-sequence-encoding region 5' and fused to the yeast ubiquitin hydrolase-encoding sequence.

17. The sequence of claim 16 wherein the signal sequence is recognized by bacterial or yeast host cells.

18. The sequence of claim 1 that is a genomic sequence.

19. The sequence of claim 3 that is covalently bound to a detectable moiety.

20. The vector of claim 9 that is a plasmid.

21. *E. coli* transformed with the vector of claim 9.

22. A methof of producing a ubiquitin hydrolase, which method comprises culturing the cells of claim 11 to express the hydrolase in the host cell culture.

23. A methof of producing a ubiquitin hydrolase, which method comprises culturing the *E. coli* of claim 21 to express the hydrolase in the *E. coli* culture.

24. The method of claim 22 further comprising the step of recovering the hydrolase from the host cell culture.

25. The method of claim 22 wherein the cells are bacterial.

* * * * *